United States Patent
Regen et al.

(10) Patent No.: US 10,322,187 B2
(45) Date of Patent: Jun. 18, 2019

(54) REDUCED TOXICITY MOLECULAR CONJUGATES OF ANTI-FUNGAL AGENTS

(71) Applicant: Lehigh University, Bethlehem, PA (US)

(72) Inventors: Steven L Regen, Bethlehem, PA (US); Vaclav Janout, Bethlehem, PA (US); Yuming Yu, Bethlehem, PA (US)

(73) Assignee: Lehigh University

( * ) Notice: Subject to any disclaimer, the term of this patent is extended or adjusted under 35 U.S.C. 154(b) by 128 days.

(21) Appl. No.: 15/233,679

(22) Filed: Aug. 10, 2016

(65) Prior Publication Data

US 2017/0042923 A1    Feb. 16, 2017

Related U.S. Application Data

(60) Provisional application No. 62/261,440, filed on Dec. 1, 2015, provisional application No. 62/203,076, filed on Aug. 10, 2015.

(51) Int. Cl.
*A61K 47/55* (2017.01)
*A61K 47/48* (2006.01)
*A61K 47/54* (2017.01)

(52) U.S. Cl.
CPC ........ *A61K 47/48123* (2013.01); *A61K 47/55* (2017.08); *A61K 47/554* (2017.08)

(58) Field of Classification Search
CPC .... A61K 31/7048; A61K 47/50; A61K 47/54; A61K 47/55; A61K 47/554; A61K 47/56; A61K 47/61; C07H 17/08
See application file for complete search history.

(56) References Cited

U.S. PATENT DOCUMENTS

| | | | |
|---|---|---|---|
| 5,606,038 A * | 2/1997 | Regen | C07H 17/08 536/6.5 |
| 8,603,999 B2 | 12/2013 | Drummond et al. | |
| 8,933,073 B2 | 1/2015 | Kellenberger | |
| 9,382,216 B2 | 7/2016 | Shukla et al. | |
| 2015/0031602 A1 | 1/2015 | Saadi et al. | |

OTHER PUBLICATIONS

Bagniski, M. et al "Amphotericin B and its new derivatives . . . " Curr. Drug Metab., vol. 10, pp. 459-469. (Year: 2009).*
Paquet, V. et al "Biologically active amphotericin B . . . " Bioconj. Chem., vol. 17, pp. 1460-1463. (Year: 2006).*
Vatmurge, N. et al "Synthesis and antimicrobial activity . . . " Bioorg. Med. Chem. Lett., vol. 18, pp. 2043-2047. (Year: 2008).*
Pore, V. et al "Design and synthesis of fluconazole/bile acid conjugate . . . " Tetrahedron, vol. 62, pp. 11178-11186. (Year: 2006).*
Anderson, TM, et al. "Amphotericin forms an extramembranous and fungicidal sterol sponge" Nat. Chem. Biol. 10(2014) 400-406.
Chen, W-H, et al. "A Fine Line Between Molecular Umbrella Transport and Ionophoric Activity" Bioconjug Chem. 20(9) (2009) 1711-1715.
Gray, KC, et al. "Amphotericin primarily kills yeast by simply binding ergosterol" Proc. Natl. Acad. Sci. U. S. A. 109(2012) 2234-2239.
Hasan, Saa, Hadjibek, SG. "Modern Conceptions about Antibiotic Levorin A and its Derivatives Action in Cell and Bilayer Lipid Membranes" International Journal of Science and Research 5 (4) (2016) 2276-2279.
Janout, V and Regen SL. "Bioconjugate-based molecular umbrellas" Bioconjugate Chem 20 (2009) 183-192.
Janout, V. et al. "Molecular Umbrella Conjugate for the Ocular Delivery of siRNA" Bioconjugate Chem 25 (2013) 197-201.
Janout, V. et al. "Molecular Umbrella-Amphotericin B Conjugates" Bioconjugate Chem. 25 (2014) 1408-1411, and Correction Bioconjugate Chem. 26 (2015) 2168-2168.
Janout, V. et al. "Taming Amphotericin B" Bioconjugate Chem. 26 (2015) 2021-2024.
Joondan N., et al. "Synthesis, micellization and interaction of novel quaternary ammonium compounds derived from L-phenylalanine and 1,2-dipalmitoyl-sn-glycerol-3-phosphocholine as model membranes in relation to their antibacterial activity and their selectivity over human red blood cells" Bioorg. Chem. 58 (2015) 117-129.
Kondo, M., Mehiri, M., Regen, S. L. "Viewing membrane-bound molecular umbrellas by parallax analyses" J. Am. Chem. Soc. 130 (2008) 13771-13777.
Legrand, P, et al. "Effects of aggregation and solvent on the toxicity of amphotericin B to human erythrocytes" Antimicrob. Agents Chemother. 36 (1992) 2518-2522.
Mehiri, M, et al. "Molecular Umbrella Transport: Exceptions to the Classic Size/Lipophilicity Rule" J Am Chem Soc. 131 (4) (2009) 1338-1339.
Pisa, D., et al. "Different Brain Regions are Infected with Fungi in Alzheimer's Disease" Scientific Reports 5:15015 (2015)1-13.
Steinbuch, KB, Fridman, M. "Mechanisms of resistance to membrane-disrupting antibiotics in Gram-positive and Gram-negative bacteria" Med. Chem. Commun. 7 (2016) 86.
Yamashita K, Janout V, Bernard EM, Armstrong D, Regen, SL. "Micelle/monomer control over the membrane disrupting properties of an amphiphilic antibiotic" J. Am. Chem. Soc. 117 (1995) 6249-6253.
Zhong Z., et al. "Cholic acid-derived facial amphiphiles with different ionic characteristics" Langmuir 21 (2005) 6235-6239.

* cited by examiner

*Primary Examiner* — Leigh C Maier
(74) *Attorney, Agent, or Firm* — The Belles Group, P.C.

(57) ABSTRACT

Compositions, compounds and methods are described for addressing both toxicity of membrane disruptive anti-microbial agents as well as poor transport of such agents across the blood-brain-barrier (BBB) via the use of molecular appendages including one or more facial amphiphiles. These molecules have in vitro anti-fungal activity that is very similar to that of the native drug but with hemolytic activity and toxicity towards mammalian cells that is greatly reduced.

11 Claims, 9 Drawing Sheets

AmB

Ergosterol

Cholesterol

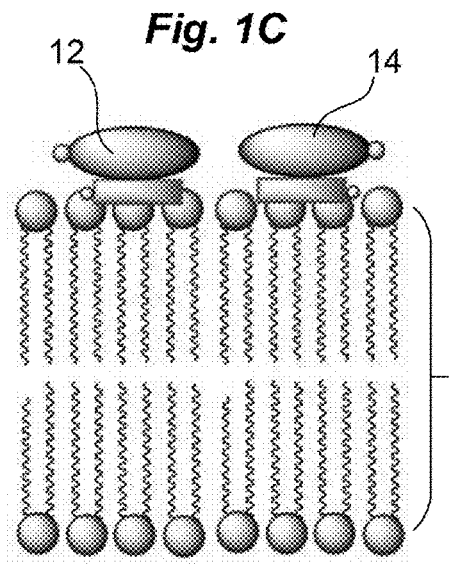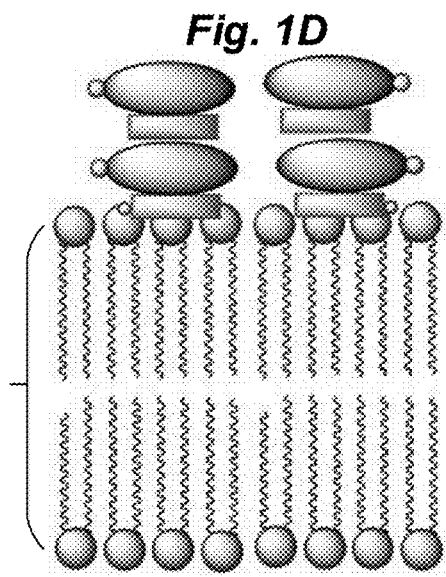

VJ-1138

REDUCED TOXICITY MOLECULAR CONJUGATES OF ANTI-FUNGAL AGENTS

CROSS REFERENCE TO RELATED APPLICATIONS

This application claims the benefit of priority from U.S. Provisional Application Ser. No. 62/203,076 filed Aug. 10, 2015 and U.S. Provisional Application Ser. No. 62/261,440, filed Dec. 1, 2015, each of which are incorporated herein by reference their entireties.

STATEMENT REGARDING GOVERNMENT INTERESTS

This work was supported in part by the following United States Government grants: R01 GM100962 from the National Institutes of Health. The Government has or may have certain rights in this invention.

FIELD OF THE DISCLOSURE

The present disclosure relates generally to methods of reducing the toxicity and improving the efficacy of drugs whose toxicity limits their use by conjugation of the drug with a facial amphiphile.

BACKGROUND

A challenging and long-standing problem has been to find ways of transporting drugs across the blood-brain barrier (BBB)—a barrier that is composed of tightly packed endothelial cells that separates circulating blood from cerebrospinal fluid (CSF) in the central nervous system (CNS). Thus, many drugs that have the potential for treating diseases of the brain are ineffective due to their limited ability to cross this barrier. Most drugs that can cross the BBB do so by passive transport—a process that usually favors small lipophilic molecules. One example of a drug whose efficacy in the CNS is limited due to poor BBB-transport is Amphotericin B (AmphB). AmphB remains the most potent fungicidal drug for the treatment of cryptococcal meningitis after over 50 years of studies in man and other animals. This success occurs despite extremely low levels of AmphB entering the cerebrospinal fluid where over a million yeast cells may reside with established cryptococcal infections. The ability to rapidly kill yeast cells in the subarachnoid space has been correlated with improved outcome. While certain lipid formulations of AmphB have improved its therapeutic to toxic ratio, they are still unable to deliver potent levels of AmphB to the subarachnoid space without dose limiting systemic toxicity. Thus, the ability to deliver significantly higher concentrations of AmphB to the subarachnoid space would be a major therapeutic advantage.

To the extent that fungal infections may contribute to other neurologic disease including Alzheimer's disease, any improvement in transport of AmphB across the BBB could have value in treating these diseases as well. Problematically, the doses required to deliver therapeutic amounts across the BBB have rate limiting systemic toxicity. As such, there remains a need for reducing the toxicity of these drugs to mammalian cells while improving selectivity and efficacy against infectious microbial agents and not compromising the ability to cross the BBB. Embodiments of the present invention provide such solutions.

SUMMARY

The methods, compounds and compositions disclosed herein provide drug conjugates that have reduced toxicity but retained anti-fungal activity compared with unconjugated counterparts. Certain examples, methods, compounds and compositions provide conjugated antifungal molecules having less toxicity than the unconjugated antifungal counterpart.

In certain embodiments, compounds are provided that include a polyene macrolide antibiotic and a molecular umbrella bound to the polyene macrolide antibiotic, the molecular umbrella including at least two facial amphiphiles bound to an amphiphile linking agent, and a non-cleavable linker bound to the amphiphile linking agent and the polyene macrolide antibiotic. In certain embodiments the polyene macrolide antibiotic is any one of amphotericin B, nystatin, mycoheptin, candicidin, perimycin, and pimaricin, or any derivative thereof. In certain examples provided herein the facial amphiphiles comprise a sterol or facially amphiphilic derivative thereof. In certain embodiments the at least two facial amphiphiles are bound to the amphiphile linker via amide bonds. In particular embodiments the sterol is any one of cholic acid, deoxycholic acid, chenodeoxycholic acid, lithocholic acid, and amphiphilic derivatives thereof.

In particular embodiments the non-cleavable linker between the amphiphile linking agent and the anti-fungal agent consists of a hydrocarbon chain. In certain embodiments the hydrocarbon chain is a $C_3$-$C_{15}$ alkyl. In other embodiments the non-cleavable linker comprises a polyether. In other embodiments the non-cleavable linker consists of a polyether. In some embodiments the the non-cleavable linker is bound to the amphiphile linking agent and the polyene macrolide antibiotic via amide bonds.

In other embodiments a compound is provided that includes a polyene macrolide antibiotic and a facial amphiphile bound to the polyene macrolide antibiotic via a non-cleavable linker. In certain embodiments the polyene macrolide antibiotic is any one of amphotericin B, nystatin, mycoheptin, candicidin, perimycin, and pimaricin, or any derivative thereof. In particular embodiments, the facial amphiphile comprises a sterol or amphiphilic derivative thereof bound to the non-cleavable linker via an amide bond. In certain embodiments provided herein, the sterol is any one of cholic acid, deoxycholic acid, chenodeoxycholic acid, lithocholic acid, and amphiphilic derivatives thereof.

In particular embodiments, the non-cleavable linker consists of a hydrocarbon chain such as a linear alkane having from 3 to 15 carbon atoms. In other embodiments the non-cleavable linker consists of a polyether. In certain embodiments, the non-cleavable linker is bound to the polyene macrolide antibiotic via an amide bond.

In some embodiments, the antifungal compound is Amphotericin B (AmphB). In certain embodiments, the reduction in toxicity is obtained by conjugation with one or more facial amphiphiles attached to a core compound having antibacterial or antibacterial activity.

In some embodiments, the methods of treating systemic fungal infections are provided by administration of an antifungal agent conjugated with a facial amphiphile. In other embodiments, compounds and compositions are provided for treatment of anti-fungal infections across the blood-brain-barrier (BBB). In some embodiments, methods and compositions are provided for treating Alzheimer's disease by administration of an antifungal agent conjugated with a facial amphiphile.

BRIEF DESCRIPTION OF THE DRAWINGS

For a more complete understanding of the present invention, including features and advantages, reference is now made to the detailed description of the invention along with the accompanying figures:

FIGS. 1A-1D depict two models of membrane disruption by AmphB as a model amphiphilic anti-microbial agent. FIGS. 1A-B, show barrel stave models in which the depicted oval molecule of AmphB combines with the depicted rectangular molecule of ergosterol to form a single pore in a lipid membrane as shown in FIG. 1A or two aligned water-filled pores as shown in FIG. 1B. FIGS. 1C-D depict a "sterol sponge" model. FIG. 1C depicts a single adsorbed complex of AmphB combined with a depicted rectangular molecule of ergosterol, while FIG. 1D depicts a "pile" of such complexes.

DETAILED DESCRIPTION

Figure 1A:
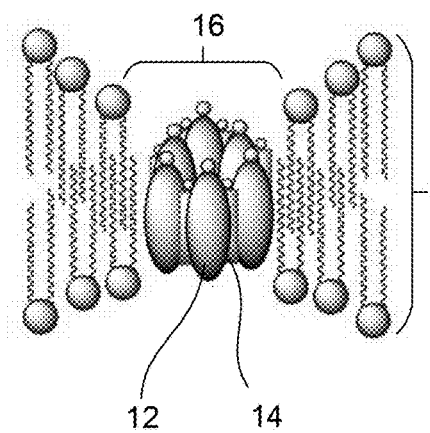

Disclosed herein are solutions addressing both toxicity of membrane disruptive anti-microbial agents as well as poor transport of such agents across the BBB via the use of molecular appendages including "molecular umbrellas" and simple "molecular floats." In certain embodiments, exemplary molecules are provided including AmphB molecular umbrella-AmphB conjugates, exemplified by, but not limited to, VJ-1138, and AmphB single amphiphile conjugates, exemplified by, but not limited to, YYM-69. In some embodiments, these compounds demonstrate in vitro antifungal activity similar to that of the native drug but with greatly reduced hemolytic activity and toxicity towards mammalian cells. In some embodiments, the solutions exemplified by the examples provided herein are applicable to those membrane-disrupting anti-fungals, including those whose toxicity may be associated with aggregated forms. The unique physical properties of the molecular appendages provided herein offer a general means of (i) enhancing the selectivity of membrane-disrupting antibiotics by suppressing the toxic action of aggregated forms on mammalian cells, and (ii) transporting drugs across the blood-brain barrier.

While the making and using of various embodiments of the present invention are discussed in detail below, it should be appreciated that embodiments of the present invention provide many applicable inventive concepts which can be employed in a wide variety of specific contexts. The specific embodiments discussed herein are merely illustrative of specific ways to make and use the invention and do not delimit the scope of the claimed invention.

ABBREVIATIONS: The following abbreviations are used throughout this application:
Amphotericin B: AmB
Blood-Brain Barrier: BBB
Critical Aggregation Concentration: CAC
Facial Amphiphile: FA
Molecular Umbrella: MU To facilitate the understanding of this invention, and for the avoidance of doubt in construing the claims herein, a number of terms are defined below. Terms defined herein have meanings as commonly understood by a person of ordinary skill in the areas relevant to the present invention. The terminology used to describe specific embodiments of the invention does not delimit the invention, except as outlined in the claims.

The terms such as "a," "an," and "the" are not intended to refer to a singular entity unless explicitly so defined, but include the general class of which a specific example may be used for illustration. The use of the terms "a" or "an" when used in conjunction with "comprising" in the claims and/or the specification may mean "one" but may also be consistent with "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group. Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily not all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result.

The terms "about" or "approximately" are defined as being close to as understood by one of ordinary skill in the art, and in one non-limiting embodiment the terms are defined to be within 10%, within 5%, within 1%, and in certain aspects within 0.5%.

Conjugates of Membrane Disrupting Drugs

Certain anti-fungal agents work by disrupting the outer membrane of the infective agents. One class of such agents are the polyene macrolide antibiotics including but not limited to AmphB (originally isolated from cultures of *Streptomyces nodosus*), nystatin (originally isolated from cultures of *Streptomyces noursei*), natamycin, also called pimaricin (originally isolated from cultures of *Streptomyces natalensis*), candicidin (originally isolated from cultures of *Streptomyces griseus*), perimycin (originally isolated from cultures of *Streptomyces coelicolor*), mycoheptin (originally isolated from cultures of *Actinomyces netropsis*), levorin (originally isolated from cultures of *Actinomyces levoris*), and derivatives thereof. The structures of these molecules is shown in Table 1 herein.

TABLE 1

Chemical structures of some of the polyene macrolide antibiotics

| Chemical Structure | Generic Name |
|---|---|
| 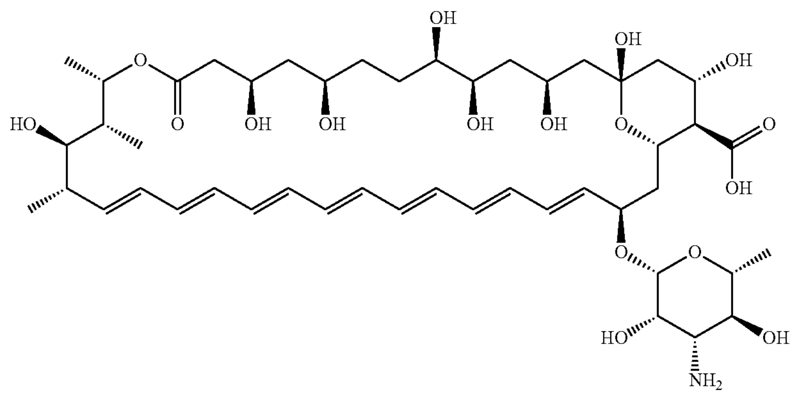 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2C(=O)O] | amphotericin B |
| 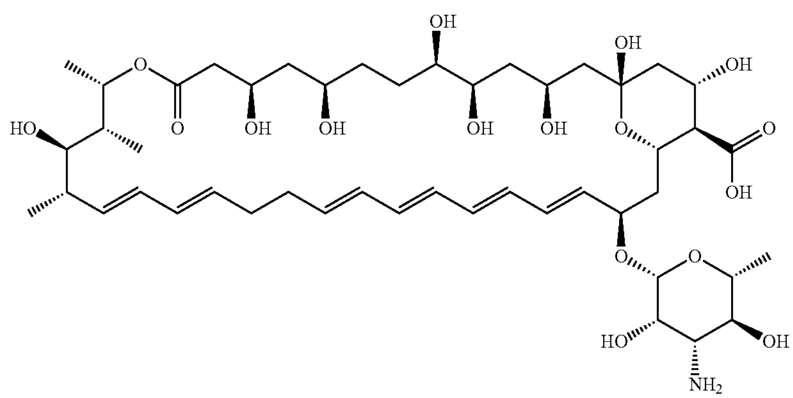 [SMILES: C[C@@H]1[C@H](O)[C@@H](C)/C=C/C=C/CC/C=C/C=C/C=C/C=C/[C@H](O[C@@H]2O[C@H](C)[C@@H](O)[C@H](N)[C@@H]2O)C[C@@H]2O[C@](O)(C[C@@H](O)C[C@@H](O)[C@H](O)CC[C@@H](O)C[C@@H](O)CC(=O)O[C@H]1C)C[C@H](O)[C@H]2C(=O)O] | nystatin |
| 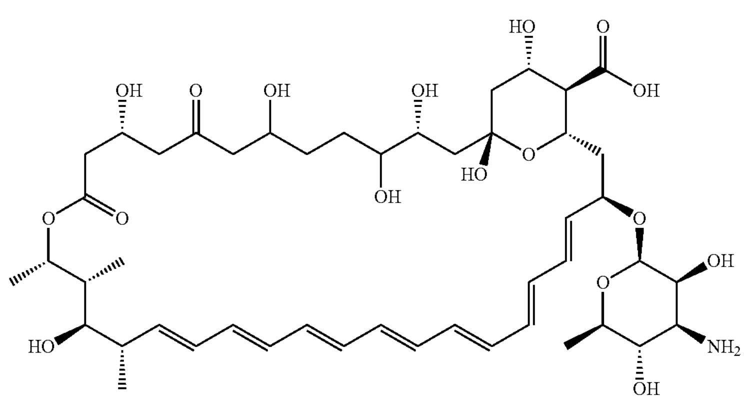 [SMILES: C[C@@H]1[C@H](O)[C@@H](C)/C=C/C=C/C=C/C=C/C=C/C=C/C=C/[C@H](O[C@@H]2O[C@H](C)[C@@H](O)[C@H](N)[C@@H]2O)C[C@@H]2O[C@](O)(C[C@@H](O)C(O)CCC(O)CC(=O)C[C@@H](O)CC(=O)O[C@H]1C)C[C@H](O)[C@H]2C(=O)O] | mycoheptin |

TABLE 1-continued

Chemical structures of some of the polyene macrolide antibiotics

| Chemical Structure | Generic Name |
|---|---|
| 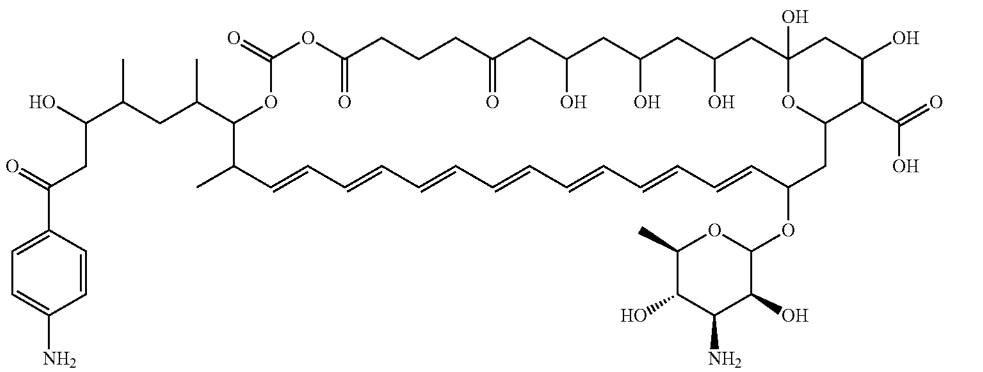 [SMILES: CC1/C=C/C=C/C=C/C=C/C=C/C=C/C=C/C(OC2O[C@H](C)[C@@H](O)[C@H](N)[C@@H]2O)CC2OC(O)(CC(O)CC(O)CC(O)CC(=O)CCCC(=O)OC(=O)OC1C(C)CC(C)C(O)CC(=O)c1ccc(N)cc1)CC(O)C2C(=O)O] | candicidin |
| 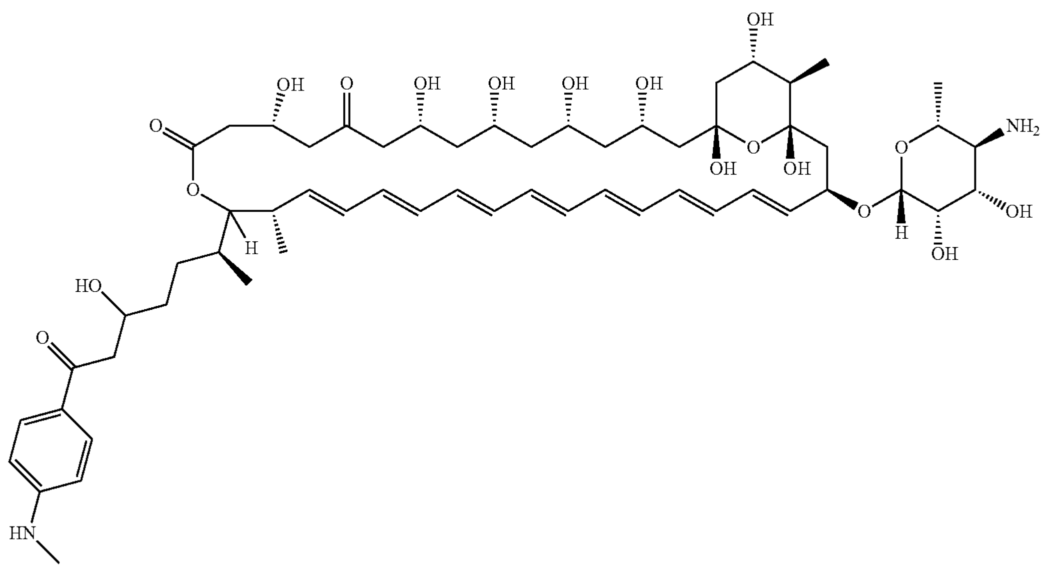 [SMILES: CNc1ccc(C(=O)CC(O)CC[C@H](C)C2OC(=O)C[C@H](O)CC(=O)C[C@H](O)C[C@H](O)C[C@H](O)C[C@H](O)C[C@]3(O)C[C@H](O)[C@@H](C)[C@](O)(C[C@@H](O[C@@H]4O[C@H](C)[C@@H](N)[C@H](O)[C@@H]4O)/C=C/C=C/C=C/C=C/C=C/C=C/C=C/[C@@H]2C)O3)cc1] | perimycin, a.k.a. aminomycin or fungimycin |
| 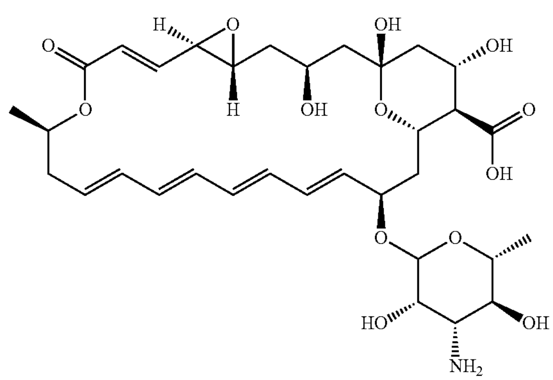 [SMILES: C[C@@H]1C/C=C/C=C/C=C/C=C/[C@H](OC2O[C@H](C)[C@@H](O)[C@H](N)[C@@H]2O)C[C@@H]2O[C@](O)(C[C@@H](O)C[C@H]3O[C@@H]3/C=C/C(=O)O1)C[C@H](O)[C@H]2C(=O)O] | pimaricin or natamycin |

Although the polyene macrolide antibiotics are effective anti-fungal agents, their considerable toxicity in humans has largely limited clinical use with the exception of AmphB and nystatin. AmphB, discovered as a natural heptaene macrolide, has been a particularly useful drug. Despite its broad use in treating fungal infections for more than 50 years, resistance to this drug has proven to be extremely rare. Although drug resistance via export mechanisms and enzymatic degradation are still possible for membrane-disrupting anti-microbials, such resistance mechanisms are likely to be less important than for those drugs that must enter the cytoplasm to exert their toxic effect.

Despite its clinical importance and its stature as the "gold standard" for anti-fungal chemotherapy, AmphB is generally regarded as one of the most toxic drugs used in modern medicine and may be lethal. Therapeutic doses of intravenously administered AmphB have been associated with multiple organ damage including severe and irreversible kidney damage.

The mechanism by which AmphB kills fungal cells continues to be debated. However, one feature that is common to all membrane-disrupting anti-fungals is that they rely heavily on hydrophobic interactions. In the case of AmphB, a special affinity towards ergosterol present in fungal membranes is believed to exist. Ergosterol (ergosta-5,7,22-trien-3β-ol) is a critical cell membrane component of fungi and protozoa that functions as the counterpart of cholesterol in animal cells. The structures of cholesterol and ergosterol are shown below:

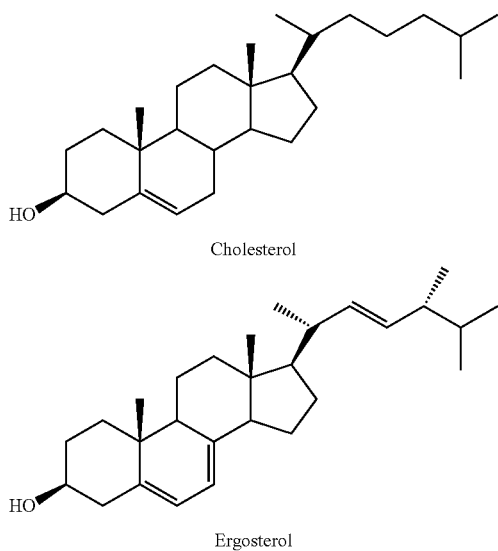

Cholesterol

Ergosterol

Figure 1B:
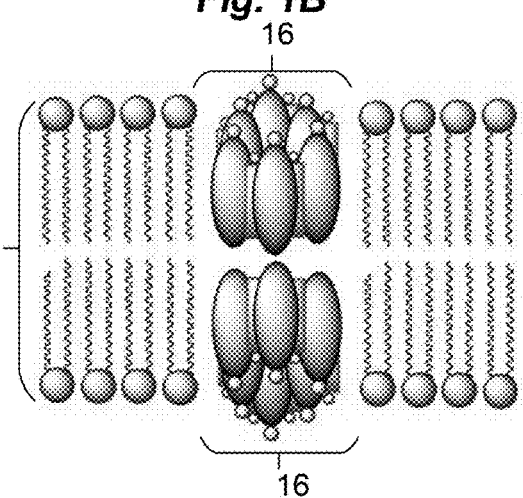

Loss of ergosterol from cell membranes results in ion leakage from the cells. In the classic barrel stave model, several AmphB molecules are proposed to combine with ergosterol to form pores. Subsequent alignment of two such pores across the plasma membrane, or a thinning of the membrane around individual pores, is thought to produce lethal water-filled channels through which ions are free to pass (FIGS. 1A and B). FIGS. 1A-B, show barrel stave models in which the depicted oval molecule of AmB (12) combines with the depicted rectangular molecule of ergosterol (14) to form a single pore (16) in lipid membrane (20) of FIG. 1A or two aligned water-filled pores (16) in FIG. 1B.

Figure 1E:
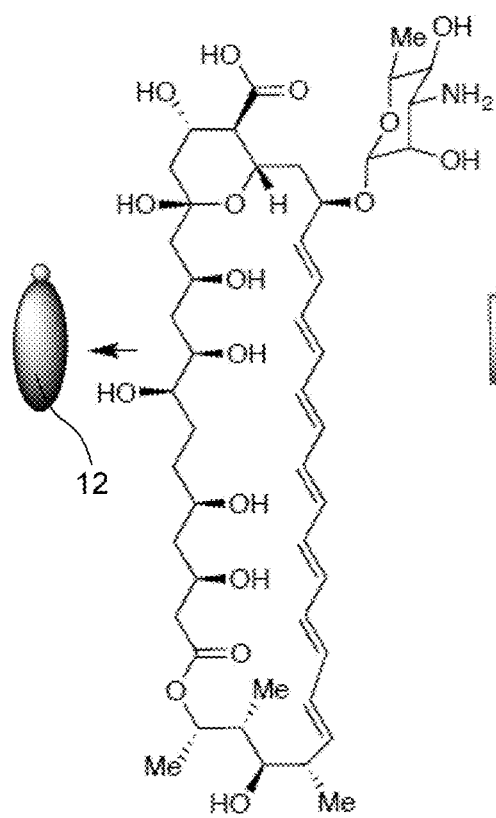
FIG. 1E shows the chemical structures of AmphB, ergosterol and cholesterol.
Figure 1E:
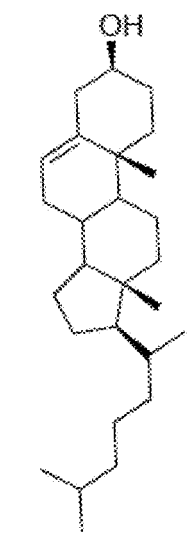

Recently, however, evidence has begun to emerge in support of an entirely different mechanism—one in which AmphB extracts ergosterol from the hydrocarbon interior of fungal membrane and deposits it on the cell's surface as a single complex or a "pile" of complexes. See e.g. Gray, K C, et al. Amphotericin primarily kills yeast by simply binding ergosterol. *Proc. Natl. Acad. Sci. U.S.A.* 109 (2012) 2234-2239; Anderson, T M, et al. Amphotericin forms an extramembranous and fungicidal sterol sponge. *Nat. Chem. Biol.* 10 (2014) 400-406. FIGS. 1C and D depict the "sterol sponge" model. FIG. 1C depicts a single adsorbed complex of AmphB (12) combined with a depicted rectangular molecule of ergosterol (14), while FIG. 1D depicts a "pile" of such complexes. FIG. 1E depicts the chemical structures of AmphB, ergosterol and cholesterol shown in FIGS. 1A-D.

What has complicated virtually all mechanistic investigations of AmphB is the fact that it exists in two discrete forms, having different biological properties. Specifically, Bolard and co-workers have shown that, whereas water-soluble aggregates of AmphB are toxic to erythrocytes and fungal cells, the monomers are toxic only to fungal cells. See Legrand, P, et al. Effects of aggregation and solvent on the toxicity of amphotericin B to human erythrocytes. *Antimicrob. Agents Chemother.* 36 (1992) 2518-2522. Similar complexity is likely to exist with all derivatives of AmphB that have been reported to date.

Recently, evidence has begun to emerge indicating that membrane-disrupting antibacterial agents can also have a strong dependency on their aggregation state; i.e., monomers exhibiting high selectivity in destroying bacteria, while aggregates show low selectivity. The present inventors have focused on the supramolecular properties of membrane-disrupting antibiotics, specifically the very different biological properties that aggregated forms of membrane-disrupting antibiotics can have as compared with their corresponding monomers. In particular, whereas monomers of AmphB are highly selective in destroying fungal cells, aggregated forms are highly toxic to both mammalian and fungal cells.

Thus, the present inventors have focused on a working hypothesis that most, if not all, of the mammalian cell toxicity associated with membrane-disrupting antibiotics is due to aggregated forms and rupture events. This has led the present inventors to identify two distinct approaches for reducing such toxicity: (i) raising the critical aggregation concentration (CAC) of the agent by chemical modification so that the monomers are favored at higher concentrations, and (ii) modifying the antibiotic in such a way that membrane rupture by attacking aggregates is prevented. The second approach is referred to herein as "taming." As used herein the term "taming" refers to a modification of a membrane-disrupting antibiotic that prevents or limits membrane rupture by aggregated forms.

In a prior study, focusing on the first approach of increasing the CAC of anti-microbial agents, certain of the present inventors provided additional evidence that AmphB monomers exhibit much greater cellular selectivity than aggregated forms by showing that the attachment of poly(ethylene glycol) chains allows one to separate antifungal from hemolytic activity. Specifically, it was shown that the attachment of poly(ethylene glycol) chains to AmphB increases its CAC, and that hemolytic activity is observed only at concentrations that are in excess of these concentrations—where aggregates and monomers coexist. Yamashita, K., et al. Micelle/monomer control over the membrane disrupting properties of an amphiphilic antibiotic. *J. Am. Chem. Soc.* 117 (1995) 6249-6253. Below their CAC concentration, where monomers are dominant, only antifungal activity was significant. This behavior closely resembles the action of a common detergent (Triton X-100) on cholesterol-rich liposomes where attack by aggregates results in a catastrophic rupture of the membrane, while attack by monomers leads to mild leakage.

This correlation between rupture/leakage and micelles/monomers suggests that the cytotoxicity of membrane-disrupting antibiotics, in general, may be due to aggregated forms. Without being bound by theory, it is believed that by raising the CAC of AmB via chemical modification, the antifungal and hemolytic activities can be separated; i.e., hemolytic activity would be observed only above its CAC; and below its CAC only antifungal activity would be found—an activity, which was similar to that of the native drug. In fact, in vivo studies of hexaethylene glycol conjugates of AmphB revealed significantly reduced toxicity. A micelle/monomer-cytotoxicity/antibacterial activity correlation has recently been found for antibacterial agents as well. Joondan N., et al. Synthesis, micellization and interaction of novel quaternary ammonium compounds derived from L-phenylalanine and 1,2-dipalmitoyl-sn-glycerol-3-phosphocholine as model membranes in relation to their antibacterial activity and their selectivity over human red blood cells. *Bioorg. Chem.* 58 (2015) 117-129. Thus, there is growing evidence that aggregated forms of membrane-disrupting antibiotics, in general, are the primary source of cytotoxicity.

In some embodiments, this dichotomy in membrane-disrupting behavior (catastrophic rupture by aggregates versus mild perturbation by monomers) can account for the reduced toxicity of AmphB that has been found with liposomal formulations; i.e., the liposomes merely serve as a reservoir that release highly cell selective monomers.

While liposomal formulations of toxic drugs such as AmphB have some utility, the present inventors have taken a different approach, that of conjugating membrane disruptive drugs with "molecular umbrellas" and "molecular floats." Molecular Umbrellas (MUs) are a unique class of amphiphiles that produce hydrophobic or hydrophilic exteriors on demand. See Janout V and Regen S L. Bioconjugate-based molecular umbrellas. *Bioconjugate Chem* 20 (2009) 183-192.

When immersed in an aqueous environment, MUs favor a conformation in which the hydrophobic faces point towards each other, leaving the hydrophilic faces and an attached hydrophilic agent exposed to the environment. However, when immersed in a lipophilic environment (e.g., the hydrocarbon interior of a lipid membrane), MUs favor a conformation in which the hydrophilic faces point towards each other, allowing them to shield an attached hydrophilic agent. In the special case of a facially amphiphilic agent (e.g., AmphB), the attached agent can exist in a partially shielded state in both hydrophilic and lipophilic environments. Without being bound by theory, it is believed that the interactions of MUs with lipid membranes is due to their unique conformational properties. The transport behavior of molecular umbrellas does not follow the classic size/lipophilicity rule; i.e., bilayer transport rates have been found to increase in certain cases with increasing numbers of umbrella walls. Also, certain MUs have been found capable of crossing the plasma membrane of HeLa cells. Thus, MUs offer an opportunity for promoting the passive transport of biologically-active agents across cell membranes in ways that have not previously been possible.

In essence, MU-active agent conjugates are composed of two or more facial amphiphiles (FA) that are attached to a central handle (Y) that connects the facial amphiphiles to the active agent (D) via a linker L according to the general formula (I):

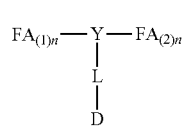

(I)

wherein $FA_{(1)n}$ and $FA_{(2)n}$ are the same or different sterol moieties that have the property of being facial amphiphiles; in certain embodiments two FA groups are included and n=1 such that the resulting structure is termed a di-sterol amphiphile if the two A groups are the same or a "mixed di-sterol" where the FA groups are different. In other embodiments, n=2 and the resulting structure is termed a tetra-sterol amphiphile;

wherein Y is a spacer connecting and providing spacing between $FA_{(1)n}$ and $FA_{(2)n}$; and wherein L is a linker (linking agent) connecting Y to active agent, D.

The combination of $FA_{(1)n}$-Y-$FA_{(2)n}$ is termed herein the "facial amphiphile backbone." In certain embodiments, $FA_{(1)}$ and $FA_{(2)}$ are selected from bile acids including cholic acid, deoxycholic acid, chenodeoxycholic acid, lithocholic acid, and amphiphilic derivatives thereof.

Cholic acid (3α,7α,12α-trihydroxy-5β-cholan-24-oic acid):

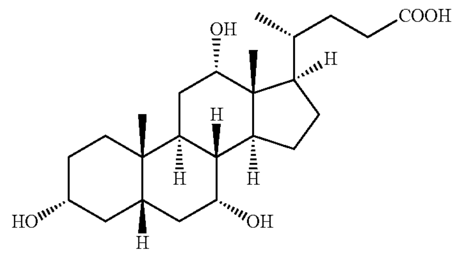

Deoxycholic acid (3α,12α-dihydroxy-5β-cholan-24-oic acid):

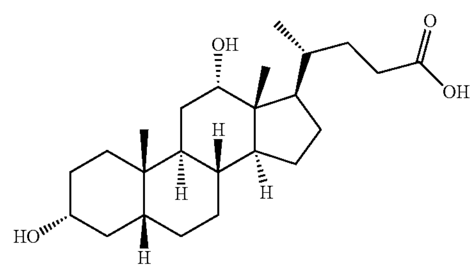

Chenodeoxycholic acid (3α,7α-dihydroxy-5β-cholan-24-oic acid):

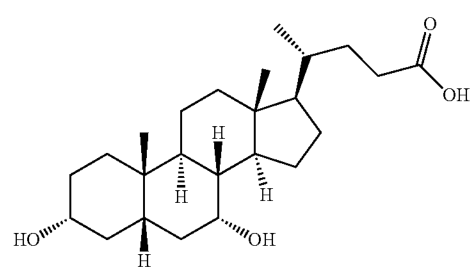

Lithocholic acid (3α-hydroxy-5β-cholan-24-oic acid):

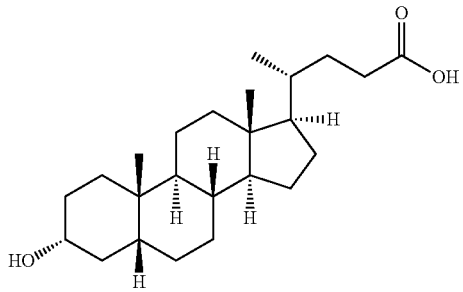

Spacings Between Two Sterols

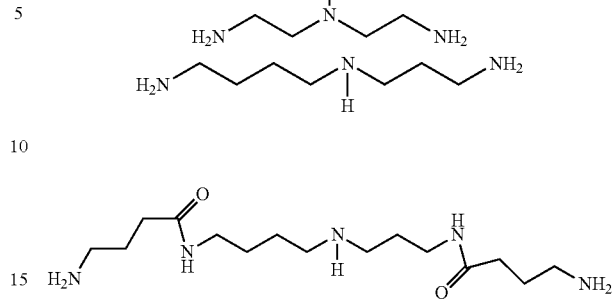

In certain embodiments, FA is a derivative of cholic acid such as for example the cholic acid derivatives (A)-(B) and (D) shown below:

In certain embodiments, spacing between the facial amphiphile backbone ($FA_{(1)n}$-Y-$FA_{(2)n}$) and the active agent

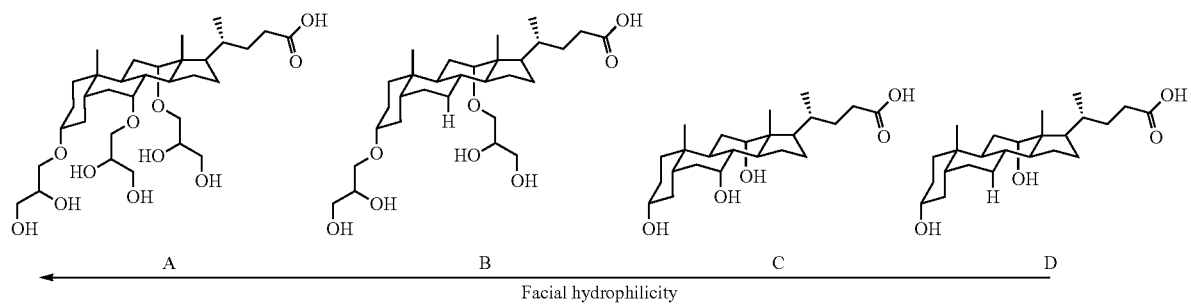

← Facial hydrophilicity

The synthesis of sterol (A), 3,7,9-tris[1-(2,3-dihydroxypropyl)-cholic acid] tris ether, above is straightforward from cholic acid (C), a.k.a. 3α,7α,12α-trihydroxy-5β-cholan-24-oic acid, and its synthesis has been described. See Zhong Z., et al. Cholic acid-derived facial amphiphiles with different ionic characteristics. *Langmuir* 21(2005) 6235-6239. In brief, the synthesis involves allylation of hydroxyl groups, conversion to a methyl ester, epoxidation of the three double bonds and hydrolysis (not shown). Sterol B, 3,7,9-tris[1-(2, 3-dihydroxypropyl)-deoxycholic acid] tris ether is prepared from deoxycholic acid (D) in a similar way. Deoxycholic acid is also known as cholanoic acid and 3α,12α-dihydroxy-5β-cholan-24-oic acid.

When making the molecular umbrellas of formula (I) above, the Y group can be selected to provide desired spacing between the two sterols (FA) such as by utilizing Y groups of various lengths as shown below in a non-limiting example:

D is provided during synthesis with a Boc-protected amine; e.g., $HO_2C(CH_2)_nNHBoc$. This spacer is then connected to a linkable drug such as for example an Amphotericin B derivative that is Fmoc protected and activated for coupling with an organic amine. If the drug has a free amino group, the spacer for connecting the facial amphiplile(s) can be a dicarboxylic acid moiety as shown below:

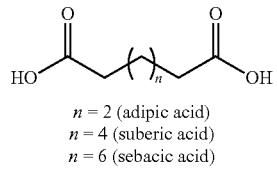

$n = 2$ (adipic acid)
$n = 4$ (suberic acid)
$n = 6$ (sebacic acid)

Initially, a series of conjugates was synthesized with a linkable form of AmphB, shown as VJ-1020 below.

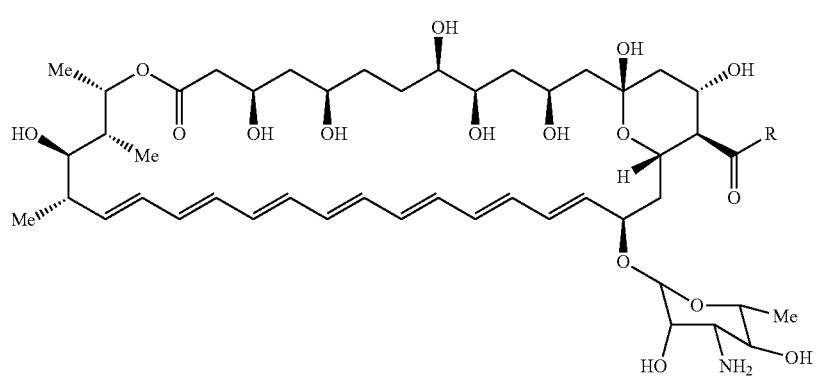

(a) Amphotericin B, R = OH [0.5/0.5/0.25/0.25]
(b) VJ-1020, R = NHCH$_2$CH$_2$SH [2/2/1/1]

An AmphB linkable derivative, molecule 1b above, exhibited reasonably high antifungal activity, having a minimum inhibitory concentration (MIC in μM) that was four times higher than AmphB against *C. albicans, C. glabrata, C. neoformans*, and *C. gatti* as shown above in brackets following the indicated molecule. Conjugates were made including tetrawalled and octawalled persulfated MUAmB conjugates containing a cleavable disulfide bond, i.e. molecule 10 below. These conjugates exhibited high water solubility, a low tendency to aggregate, negligible hemolytic activity at 100 μM, and an ability to release 1(b) above under reducing conditions.

lung tissue, after intravenous administration of 10 above, showed negligible activity. These results suggest that 1(b) was not being released from the molecular umbrella in vivo and was otherwise ineffective.

These results prompted synthesis of simpler, non-cleavable MU-AmB conjugates. At that time, it also occurred to the inventors that such non-cleavable conjugates might exhibit exceptional selectivity in destroying fungal cells. Specifically, it was envisioned that the cytotoxicity of aggregated forms might be suppressed due to the presence of the umbrella framework.

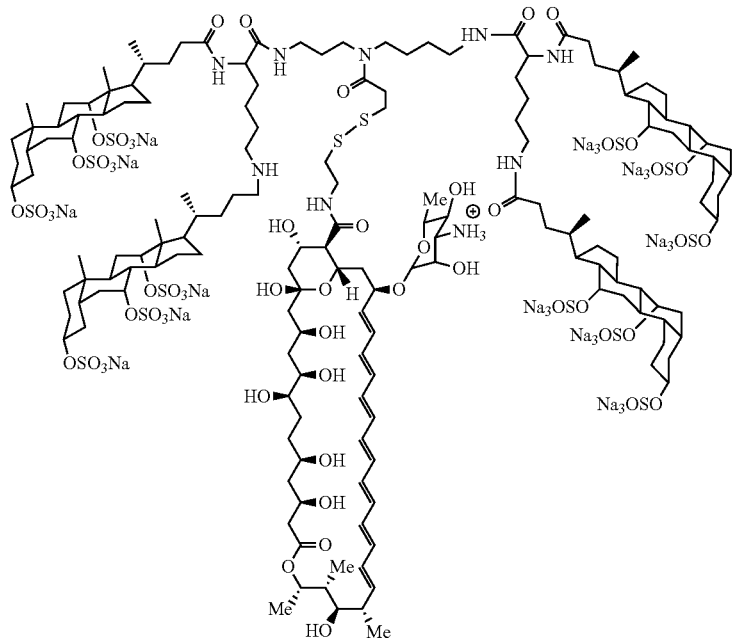

However, in vivo studies showed that these conjugates had negligible antifungal activity (kidney tissue assay in mice). It was determined that the minimum inhibitory concentration (MIC in μM) relative to AmphB against *C. albicans, C. glabrata, C. neoformans*, and *C. gatti* was [>426/>426/>426/>426]. In addition, analysis of brain and With these ideas in mind, a broad series of non-cleavable MU-AmB conjugates was synthesized and tested for antifungal activity and reduced toxicity. Several of these conjugates are shown in Table 2 below, including the minimum inhibitory concentration (MIC in μM) against *C. albicans*,

*C. glabrata, C. neoformans*, and *C. gatti* shown in brackets following the indicated molecule:

TABLE 2

AmphB Conjugates

| Chemical Structure | Name and formula |
|---|---|
|  | VJ-1138, R = H<br>[2/4/2/3] |

TABLE 2-continued

AmphB Conjugates

| Chemical Structure | Name and formula |
|---|---|
|  | VJ-1147, R = CONH(CH$_2$)$_4$NH$_2$ [8/16 /8/8] |

TABLE 2-continued

| Chemical Structure | Name and formula |
|---|---|
| 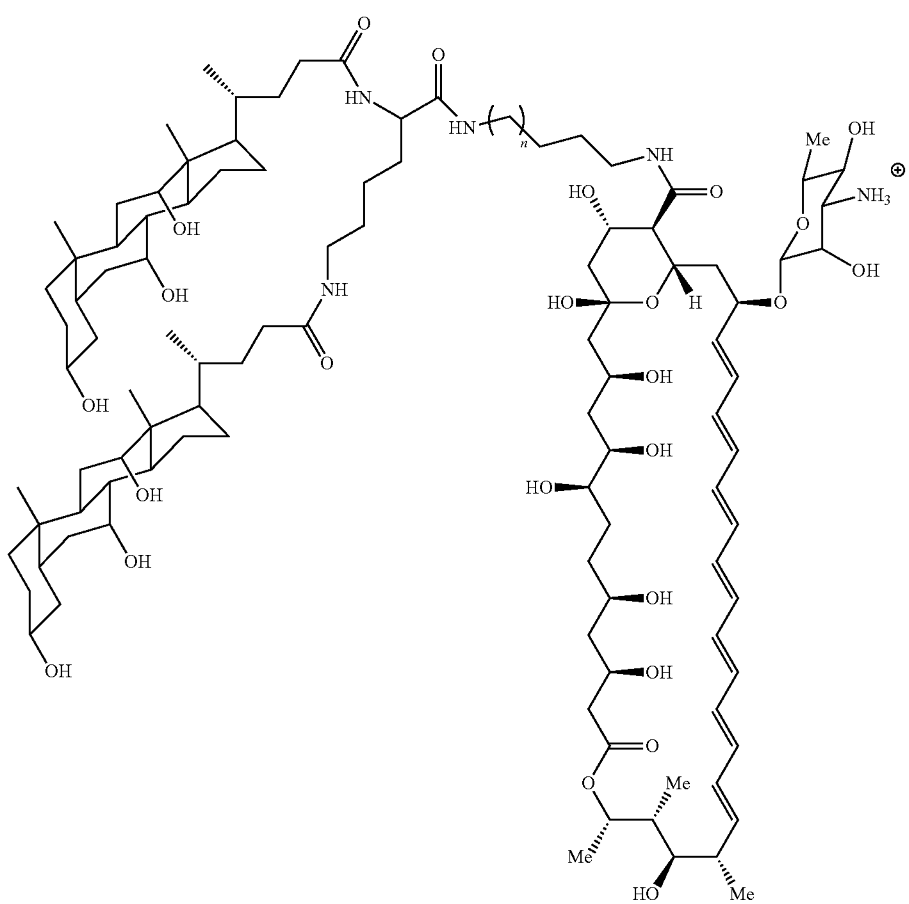 | YM-15, n =1<br>[>16/>16/>16/4] |

TABLE 2-continued
AmphB Conjugates
| Chemical Structure | Name and formula |
|---|---|
| 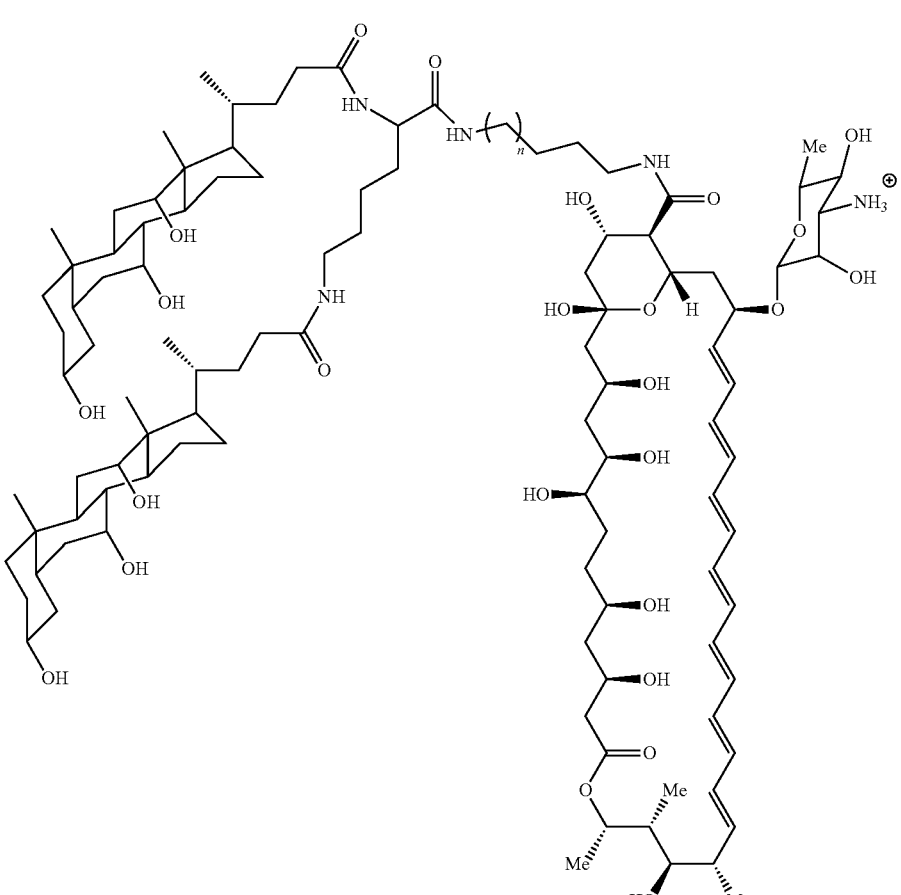 | YM-14, n = 3<br>[>16/>16/>16/>16] |

TABLE 2-continued

AmphB Conjugates

| Chemical Structure | Name and formula |
|---|---|
| 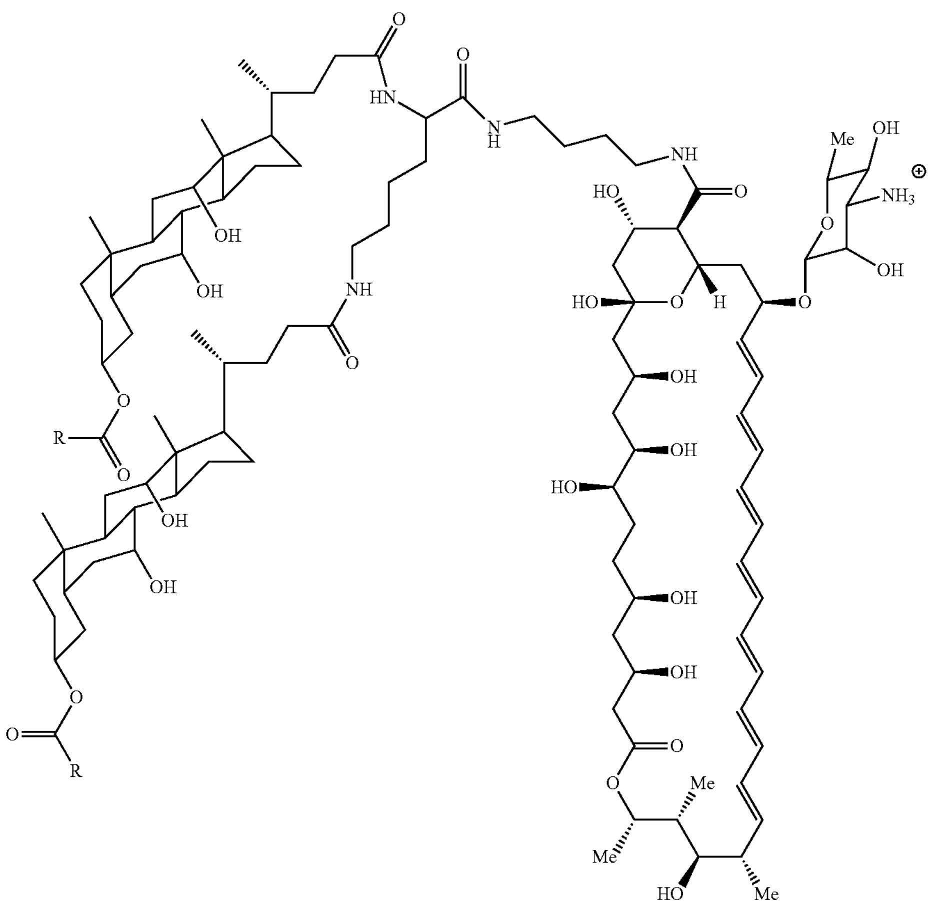 | YM-18, R = NH(CH$_2$)$_4$NH$_2$ [2/16/2/2] |

TABLE 2-continued

AmphB Conjugates

| Chemical Structure | Name and formula |
|---|---|
| 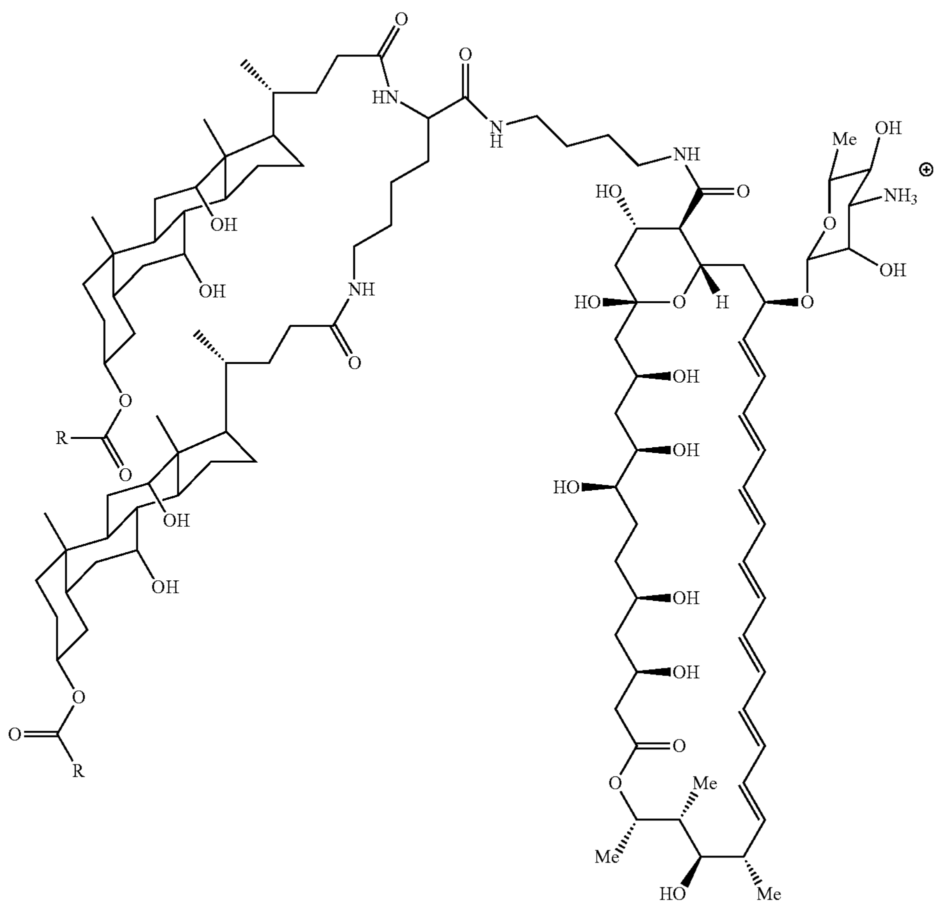 | YM-19,<br>R = NH(CH$_2$)$_2$N(CH$_3$)$_2$<br>[4/32/2/2] |

TABLE 2-continued

AmphB Conjugates

| Chemical Structure | Name and formula |
|---|---|
| 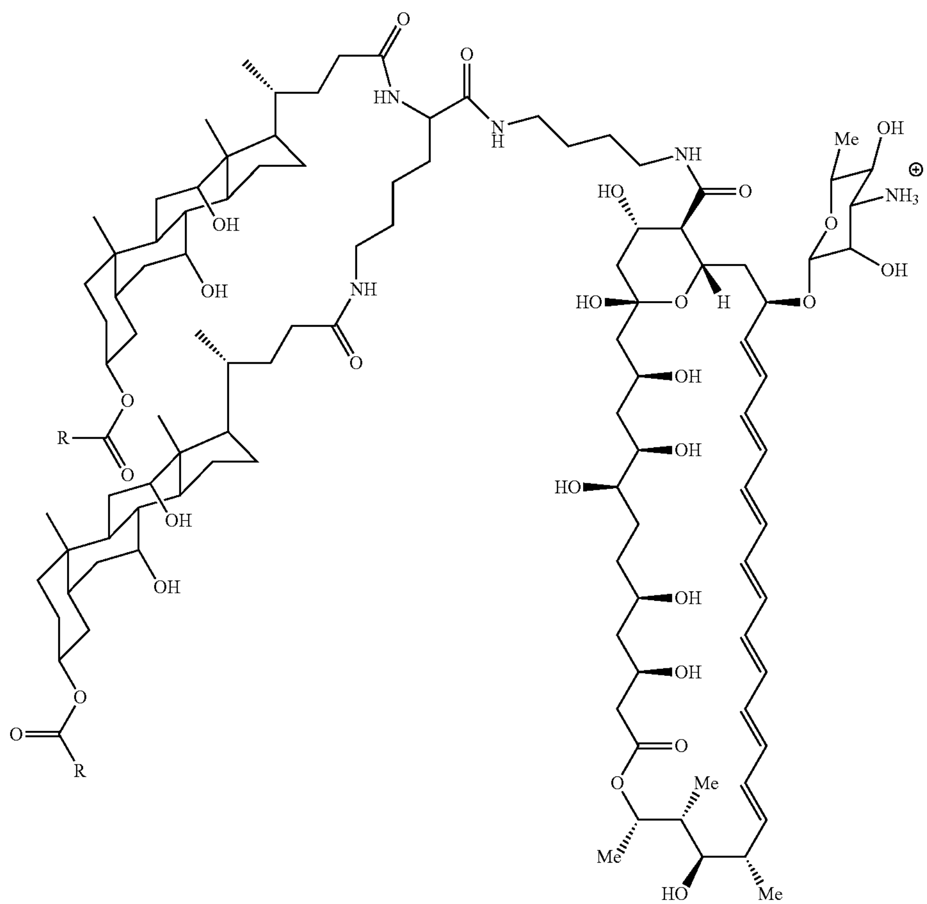 | YM-13<br>R = NHCH$_2$(CHOH)$_4$CH$_2$OH<br>[8/8/2/4] |

TABLE 2-continued

AmphB Conjugates

| Chemical Structure | Name and formula |
|---|---|
| | YM-42 [>16/>16/>16/>16] |

Figure 3:
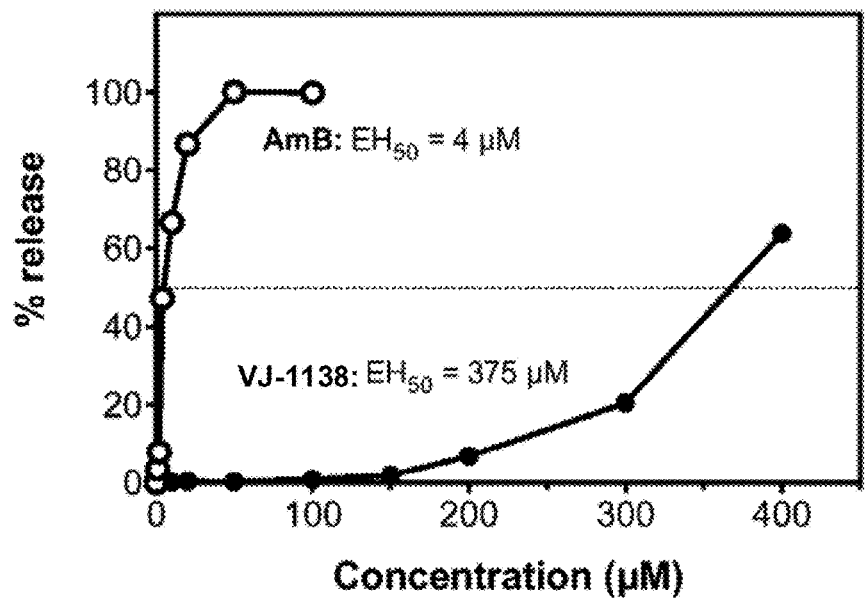
FIG. 3 compares the hemolytic activity of AmphB versus conjugate (VJ-1138) at various concentrations.
Figure 4:
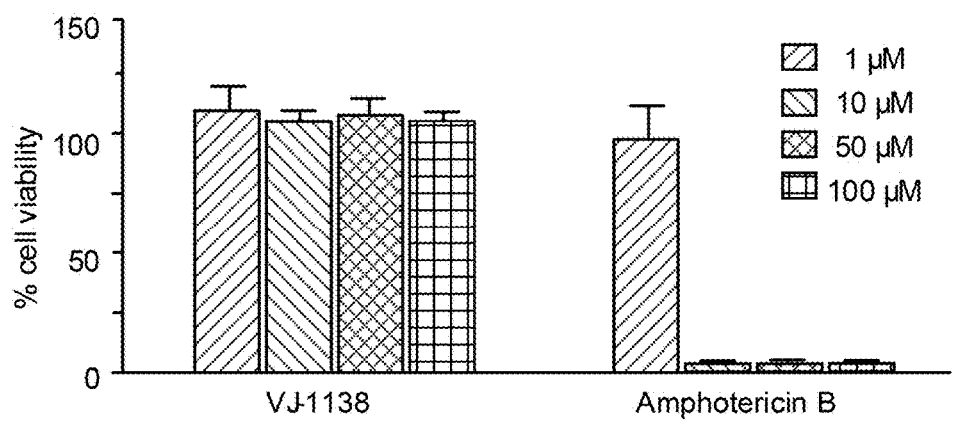
FIG. 4 compares the toxicity of AmphB versus AmphB conjugate (VJ-1138) against HEK293 kidney cells.

One of the simplest of the above conjugates (VJ-1138) showed antifungal activity approaching that of AmphB but with dramatically reduced hemolytic activity and cytotoxicity toward mammalian cells as shown in FIGS. 3 and 4, respectively.

The preference that molecular umbrellas have for residing at the membrane surface also provides an opportunity for reducing the cytotoxicity of membrane-disrupting antibiotics by preventing high local concentrations (i.e., aggregated forms) from inserting into cell membranes.

Dosage and Formulation

When administered for the treatment or inhibition of a particular disease state or disorder, it is understood that the effective dosage may vary depending upon the particular compound utilized, the mode of administration, the condition, and severity of the condition being treated, as well as the various physical factors related to the individual being treated. Effective administration of the compounds of this invention may be given at an oral or intravenous dose of from about 0.1 mg/day to about 1,000 mg/day. The projected daily dosages are expected to vary with route of administration, the weight of the patient and underlying conditions.

Such doses may be administered in any manner useful in directing the active compounds herein to the recipient's bloodstream, including orally, via implants, parentally (including intravenous, intraperitoneal, intraarticularly and subcutaneous injections), rectally, intranasally, topically, ocularly (via eye drops), vaginally, and transdermally.

Oral formulations containing the compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

Useful tablet formulations may be made by conventional compression and wet granulation or dry granulation methods, and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar.

Suitable surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine.

Oral formulations herein may utilize standard delay or time release formulations to alter the absorption of the active compound(s). In some embodiments, the oral formulation may also consist of administering the active ingredient in water or a fruit juice, containing appropriate solubilizers or emulsifiers as needed.

In some embodiments, it may be desirable to administer the compounds directly to the airways in the form of an aerosol.

In some embodiments, compounds of the present invention may also be administered parenterally or intraperitoneally. Solutions or suspensions of these active compounds as a free base or pharmacologically acceptable salt can be prepared in water suitably mixed with a surfactant such as hydroxypropyl cellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

As used in accordance with this invention, the term "providing," with respect to providing a compound or substance covered by this invention, means either directly administering such a compound or substance, or administering a prodrug, derivative, or analog that will form the effective amount of the compound or substance within the body.

The reactions of the processes described herein can be carried out in air or under an inert atmosphere. Typically, reactions containing reagents or products that are substantially reactive with air can be carried out using air-sensitive synthetic techniques that are well known to the skilled artisan.

Upon carrying out preparation of compounds according to the processes described herein, the usual isolation and purification operations such as concentration, filtration, extraction, solid-phase extraction, recrystallization, chromatography, and the like may be used to isolate the desired products.

The invention will be described in greater detail by way of specific examples. The following example is offered for illustrative purposes, and are not intended to limit the invention in any manner. Those of skill in the art will readily recognize a variety of noncritical parameters which can be changed or modified to yield essentially the same results.

EXAMPLES

Example 1: Toxicity Taming Using Molecular Umbrellas

Prior fluorescence quenching measurements by certain of the present inventors provided support for a mechanism of the killing of fungal cells by the "sponge" mechanism. See Kondo, M., Mehiri, M., and Regen, S. L. Viewing membrane-bound molecular umbrellas by parallax analyses. *J. Am. Chem. Soc.* 130 (2008) 13771-13777. In these studies, diwalled and tetrawalled "molecular umbrellas" bearing Cascade blue; i.e., 1b and 2b, respectively of Table 3 below were generated where the Y=Cascade blue. These measurements provided support for a model in which such molecules favor binding at the surface as opposed to the interior of lipid membranes. The present inventors posited that analogous molecules bearing AmphB would localize a pendant AmphB moiety close to the cell surface, thereby favoring the killing of fungal cells via a "sponge" mechanism in which the AmphB soaks ergosterol out of the lipid membrane causing membrane failure of fungal and protozoal cells.

In some embodiments, molecular umbrella-AmphB conjugates are according to Table 3 below:

TABLE 3
Examples of Molecular Umbrellas of Amph B and Cascade Blue
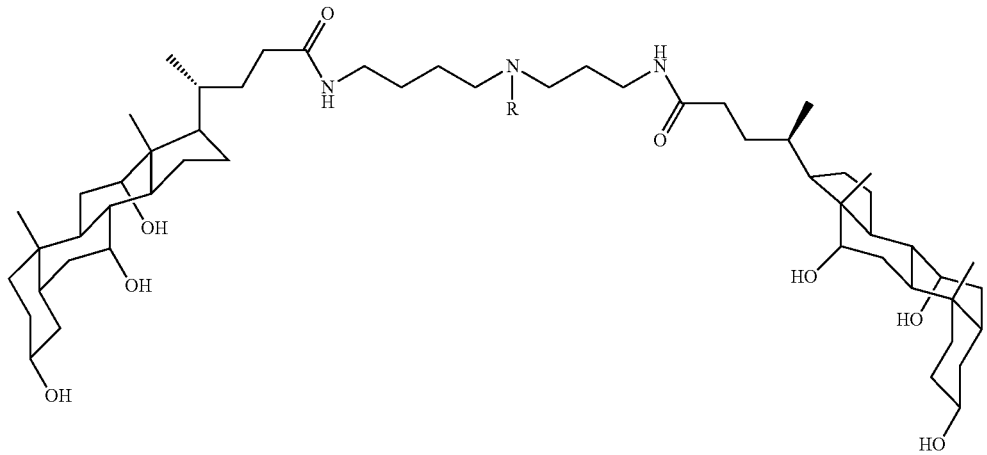
1a, R = X
b, R = Y
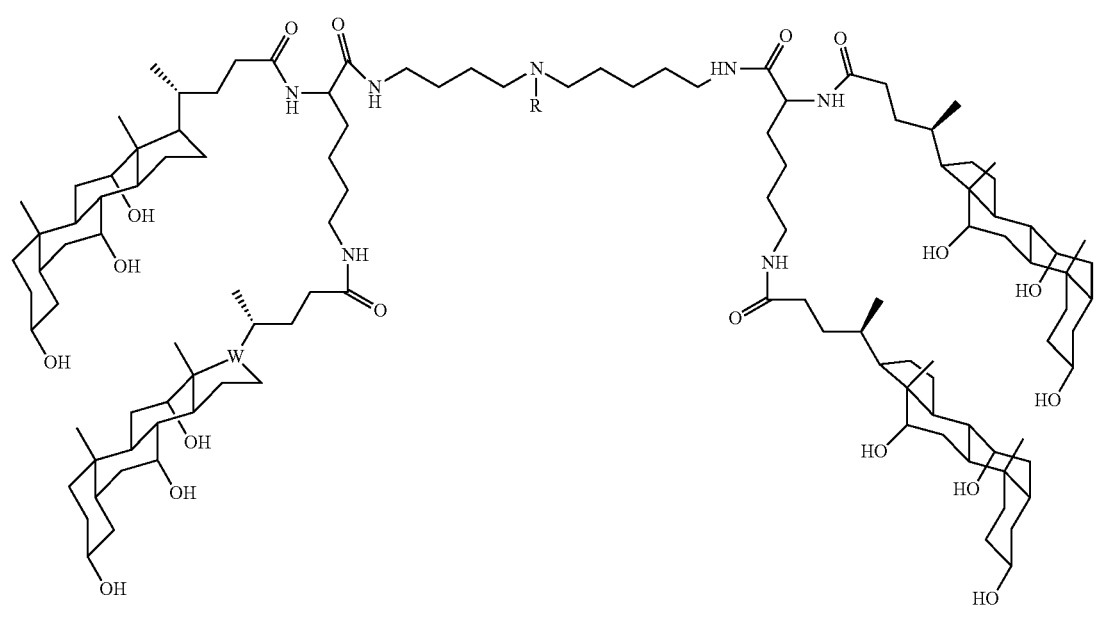
2a, R = X
b, R = Y
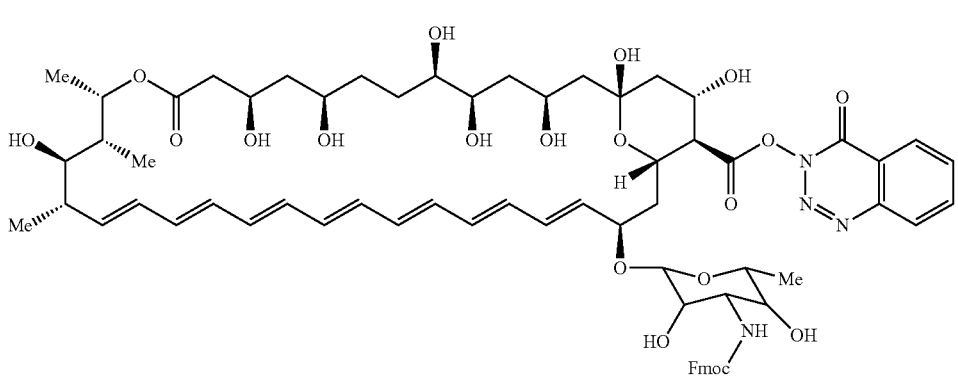
3

TABLE 3-continued

Examples of Molecular Umbrellas of Amph B and Cascade Blue

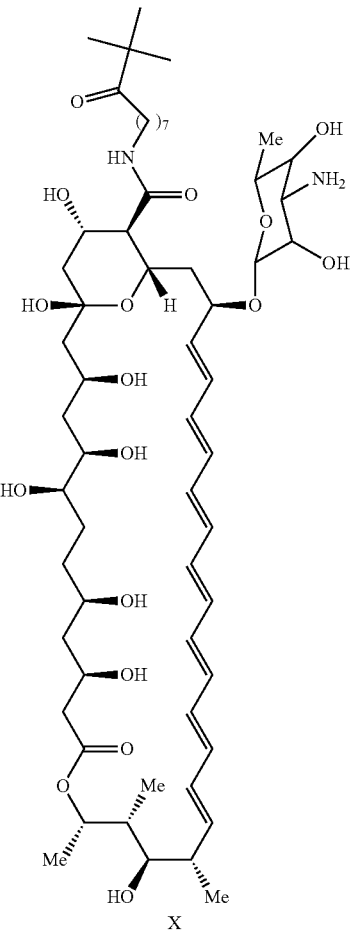

X

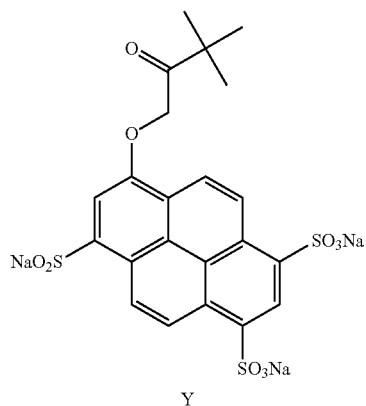

Y (Y) is Cascade Blue. (X)=an AmphB pendent group resulting from coupling to a diwalled molecular umbrella 1a above and a tetrawalled molecular umbrella in 2a above. Thus, direct coupling of 3 above with a diwalled molecular umbrella bearing a pendant amine group IV of Scheme 1 below, followed by removal of Fmoc with piperidine affords VJ-1138 of Table 2. Direct coupling of 3 above with a tetrawalled molecular umbrella analog, followed by removal of Fmoc with piperidine affords VJ-1155 (2a) Table 3.

In brief, and described in further detail in the following synthetic procedures section of this Example, in synthesizing the above derivatives of AmphB, an Fmoc-carbamate of AmphB that was been activated by N,N,N',N'-tetramethyl-O-(3,4-dihydro-4-oxo-1,2,3-benzotriazin-3-yl)-uronium tetrafluoroborate (TDBTU) was found to be a stable precursor for molecular conjugates.

Scheme 1:

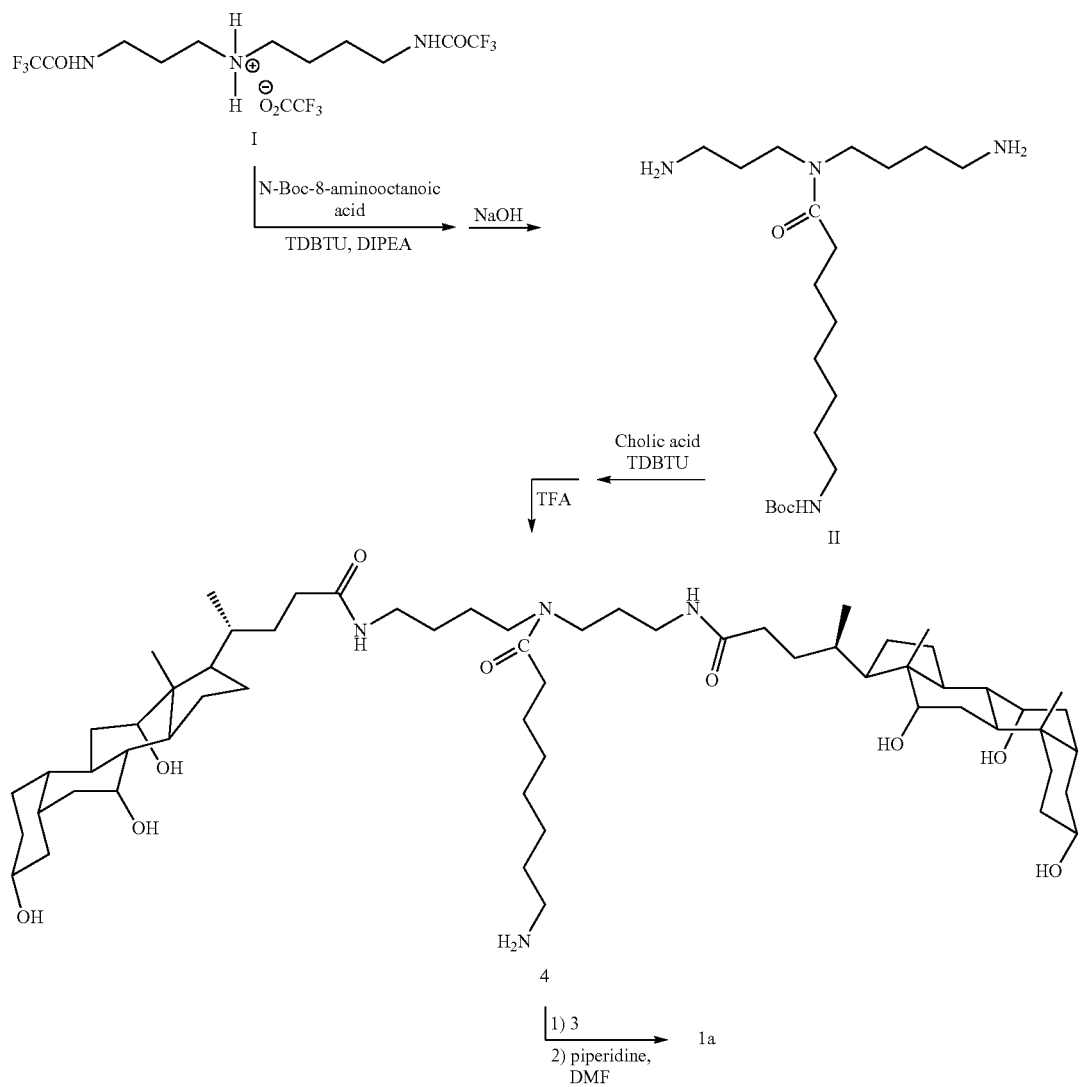

A similar sequence of reactions was carried out using lysine dicholamide in place of cholic acid afforded VJ-1147 of Table 2. To assess the antifungal properties of the diwalled VJ-1138 (Table 2) and 2a of Table 3, their in vitro activities were examined against four clinically relevant microbes, i.e., *C. albicans, C. glabrata, C. neoformans*, and *C. gatti* (Table 4).

TABLE 4

Antifungal Activities

| Microbe | MIC/MFC* (μM) | | |
|---|---|---|---|
| | AmB | VJ-1138 (1a) | 2a |
| C. albicans | 0.5/1 | 1/2 | >11/— |
| C. glabrata | 0.5/1 | 2/4 | >11/— |
| C. neoformans | 0.3/0.5 | 1/2 | >11/— |
| C. gatti | 0.3/0.5 | 1/2 | >11/— |

*MIC and MFC values are the lowest concentrations required for completely inhibiting growth, and killing at least 99% of the fungi, respectively.

On a molar basis, VJ-1138 exhibits a potency that approaches that of the native antibiotic. The tetrawalled VJ-1155 (2a of Table 3) showed no antifungal activity at 11 μM. Further studies on VJ-1138 were undertaken as one example of the molecules of Table 2 to determine whether the conjugated form of AmphB has a reduced tendency to aggregate.

Figure 2A:
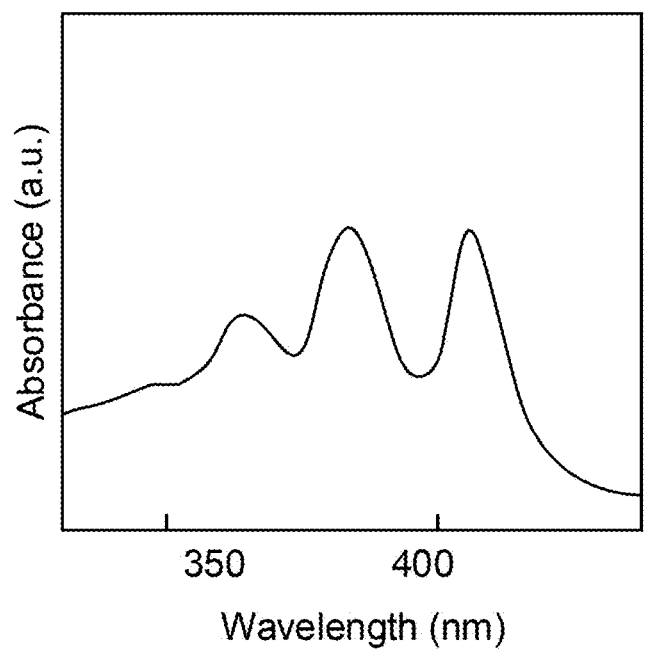
FIG. 2A shows an absorption spectrum of a diwalled molecular umbrella conjugate of AmphB (VJ-1138).

Similar to AmphB, VJ-1138 exhibits a characteristic absorption at 409 nm as shown in FIG. 2A, with an apparent molar absorptivity that decreases upon aggregation. If one lets: (i) T, m, and P represent the total, the monomeric, and the aggregate concentrations of this macrolide, respectively; (ii) ε represent the apparent molar absorptivity; and (iii) εm and εp represent the molar absorptivity for the monomeric and aggregate components, respectively, then it can be shown that ε=εp+(εm−εp)m/T. See Yamashita K, Janout V, Bernard E M, Armstrong D, and Regen, S L. Micelle/monomer control over the membrane disrupting properties of an amphiphilic antibiotic. *J. Am. Chem. Soc.* 117 (1995)

Figure 2B:
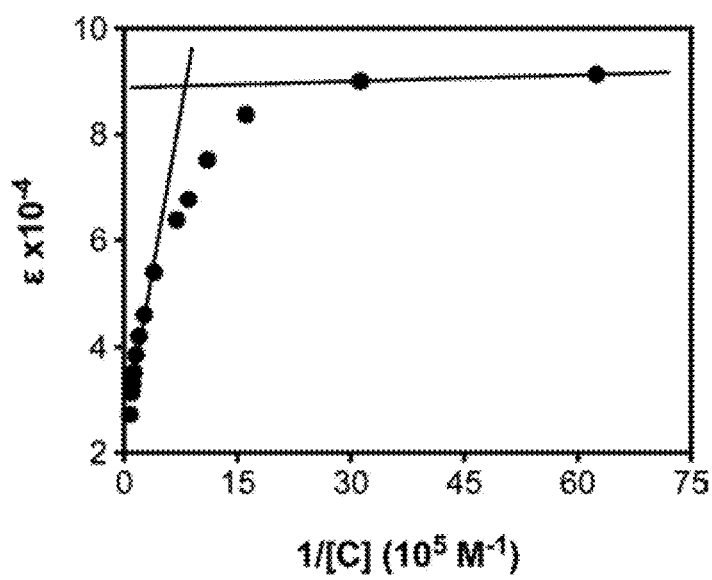
FIG. 2B shows a plot of molar absorptivity ($\lambda_{max}$ 409 nm) as a function of the reciprocal concentration of VJ-1138 in PBS at 37° C.

6249-6253. At concentrations that are in excess of its CAC, m is constant, and ε is expected to be inversely proportional to T. Thus, by measuring the apparent molar absorptivity as a function of the reciprocal of the concentration of VJ-1138, its CAC value is estimated to be 0.9 µM (from the intercept of two straight lines). This is essentially the same CAC as that of AmphB as shown in FIG. 2B, which presents a plot of molar absorptivity ($\lambda_{max}$ 409 nm) as a function of the reciprocal concentration of 1a [C] in PBS at 37° C.

Significantly, aggregates of VJ-1138 showed dramatically reduced hemolytic activity relative to aggregates of AmphB as shown in FIG. 3, which presents a plot of percent release of hemoglobin from sheep red blood cells as a function of concentration of AmphB (○) and 1a (•) at 37° C. in saline, pH 7.4. Thus, whereas the concentration of AmphB that was required to induce 50% release of hemoglobin from erythrocytes ($EH_{50}$) was 4 µM, the concentration of VJ-1138 (1a) that was required for such release was approximately 2 orders of magnitude higher, i.e., an $EH_{50}$ of 375 µM.

As further evidence that AmphB has been tamed in the form of VJ-1138 (1a), its toxicity toward HEK293t cells was compared with that of the native AmphB molecule. FIG. 4 presents toxicity data as a bar graph showing the viability HEK293t cells in the presence of 1, 10, 50, and 100 µM concentrations of AmB and VJ-1138 (1a). As shown in FIG. 4, the toxicity of the conjugate toward these cells has been dramatically reduced.

In a broader context, the taming strategy described herein offers a unique opportunity for enhancing the cellular selectivity and therapeutic potential of a variety of membrane disrupting agents. Such agents operating at the membrane level are particularly attractive as drugs because they are likely to circumvent two of the more common mechanisms of drug resistance to a significant extent, i.e., export mechanisms and enzymatic degradation within the cell. The ability of molecular umbrellas to cross lipid membranes raises the possibility that molecules such as exemplified by VJ-1138 may allow for more efficient transport of this heptaene macrolide antibiotic across the blood-brain-barrier via passive diffusion.

Example 2: Synthetic Procedures and Analytical Techniques

Medium pressure liquid chromatography was performed using an Isolera One system equipped with a dual wavelength UV detector from Biotage and Biotage SNAP Ultra columns. For purification via preparative TLC, silica gel plates (EMD, 1 mm, 20×20 cm) were used, which contained a fluorescence indicator F254. Column chromatography was carried out using silica gel 60, EMD Millipore. All solvents were purchased from EMD Millipore Corporation and used as obtained. Deionized water was purified by a Millipore Milli-Q filtering system equipped with one carbon and two ion-exchange stages. All mass spectral measurements were performed by an Agilent LC-TOF high resolution TOF analyzer at the University of California-Riverside. All NMR spectra were recorded on a Bruker Avance 500 MHz instrument. Residual solvent signals were used as a reference. All UV measurements were performed on a Cary 300 Bio spectrometer from Varian.

Synthesis of $N_2$-(Boc-8-aminocapryloyl)-spermidine amide (II) of Scheme 1

$N_2$-(Boc-8-aminocapryloyl)-$N_1$,$N_3$-(trifluoroacetyl)spermidine triamide was synthesized in the following way: To a solution that was made from 271 mg (0.600 mmol) of spermidine $N_1$,$N_3$-bistrifluoroacetamide, TFA salt (I), 1.0 mL of DMF and 304 µL of N,N-diisopropylethylamine (1.90 mmol) (Sigma-Aldrich) was added a solution made from 0.155 g (0.600 mmol) of 8-Boc aminocaprylic acid (Chem-Impex Intl.), 1.5 mL of DMF, 229 mg (0.604 mmol) of O-(benzotriazol-1-yl)-N,N,N',N'-tetramethyl uronium hexafluorophosphate (HBTU, Sigma-Aldrich), and 0.106 mL (0.612 mmol) of N,N-diisopropylethylamine. After the resulting mixture was stirred in closed flask at room temperature (rt) for 17 h, the volatiles were removed under reduced pressure (10 Torr, 45° C.). To the crude product mixture was added 30 mL of dichloromethane. The resulting solution was then washed, sequentially, with 5 mL of 0.5 M aqueous HCl, 5 mL of 2% $NaHCO_3$, and three times with 5 mL of $H_2O$, and then dried over anhydrous $Na_2SO_4$. Additional purification was carried out using a medium pressure gradient column chromatography (Isolera, Snap Ultra, 10 g, dichloromethane/isopropyl alcohol, 100/8 to 5/1, v/v) affording 0.265 g (76%) of $N_2$-(Boc-8-aminocapryloyl)-$N_1$, $N_3$-(trifluoroacetyl) spermidine triamide having $R_f$ 0.65 (dichloromethane/isopropyl alcohol, 5/1, v/v) and $^1$H-NMR (MeOD): 3.28-3.40 (m, 8H); 2.99 (t, 2H); 2.33 (m, 2H); 1.77 (m, 2H); 1.54 (m, 8H); 1.40 (s, 9H); 1.32 (m, 6H).

Hydrolysis of $N_2$-(Boc-8-aminocapryloyl)-$N_1$,$N_3$-(trifluoroacetyl)spermidine triamide of Scheme 1

A solution was prepared from methanol (4.0 mL), 0.250 g (0.431 mmol) of this bistrifluoroaceamide and 0.890 mL of 1N NaOH. After stirring this solution for 16 h at rt, the solvents were removed under reduced pressure (10 Torr, 35° C.). The crude product was then dissolved in 15 mL of dichloromethane and washed three times with 2 mL of $H_2O$. The dichloromethane was then removed under reduced pressure and the product dried (0.5 Torr, rt, 24 h) to give 0.155 g (95%) of the spermidine derivative II, having $^1$H-NMR ($CD_3OD$, ppm): 3.29-3.43 (m, 4H); 3.00 (t, 2H); 2.57-2.67 (m, 4H); 2.37 (t, 2H); 1.53-1.75 (m, 6H); 1.49-1.52 (m, 4H); 1.42 (s, 9H); 1.32 (m, 6H).

Synthesis of $N_1$,$N_3$-dicholeamido-$N_2$-(Boc-8-aminocapryloyl) spermidine amide (IV) of Scheme 1

A solution was prepared from 46.4 mg (39.6 µmol) of $N_1$,$N_3$-dicholeamido-$N_2$-(Boc-8-aminocapryloyl) spermidine amide (III), 2.5 mL of chloroform and 0.25 mL of trifluoroacetic acid and stirred in a closed flask for 2 h at rt.

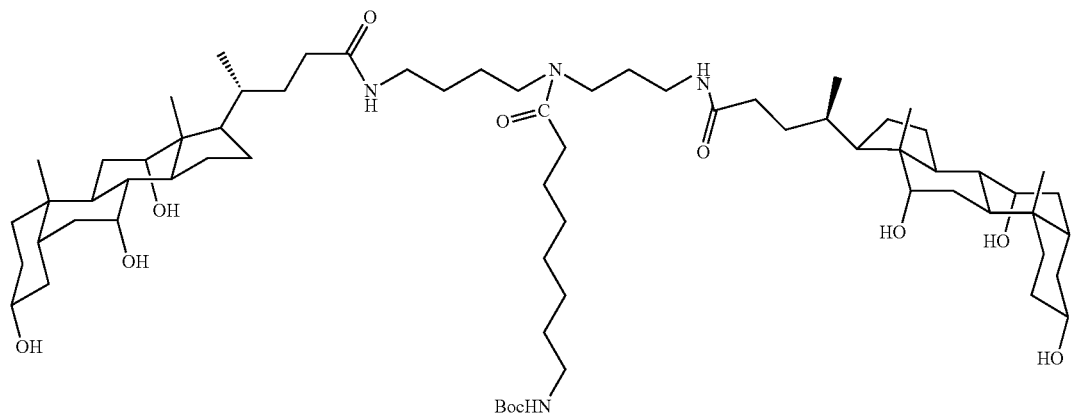

III

The solvents were then removed under reduced pressure affording 46.3 mg of crude product. This product was then dissolved in 2.0 mL of methanol. To this methanolic solution was then added 0.280 mL of 1N aqueous NaOH and the solution stirred at rt for 1 h. The solvents were then removed under reduced pressure, and the crude product dried (1 Torr, rt, 16 h). The resulting solid was triturated four times using 10 mL of H₂O and dried (1 Torr, rt, 4 h) to give 42.4 mg (99%) of the free amine (IV) having ¹H-NMR (CD₃OD, ppm): 3.92 (s, 2H); 3.76 (s, 2H); 3.20-3.43 (m, 6H); 3.17 (m, 4H); 2.92 (m, 2H); 0.83-2.38 (m, 78H); 0.69 (s, 6H).

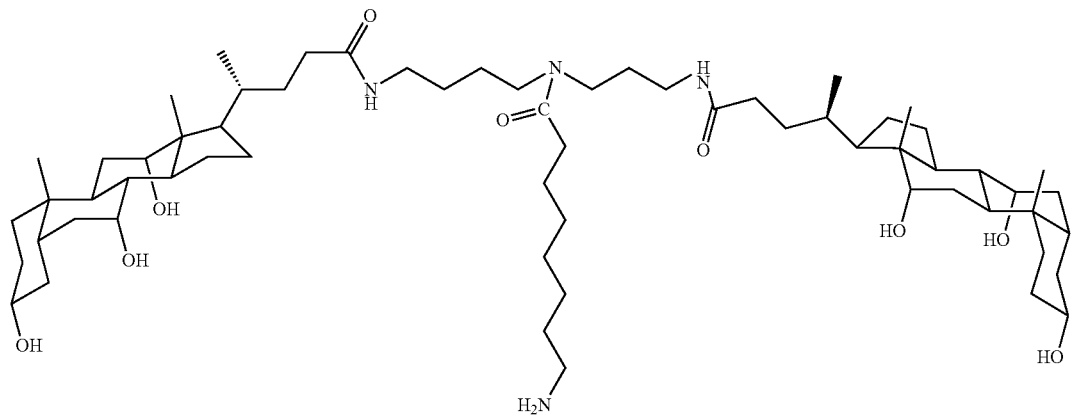

IV

Synthesis of N-Fmoc Amphotericin B carbamate, (3,4-dihydro-4-oxo-1,2,3-benzotriazin-3-yl) ester (VII)

(N,N,N',N'-Tetramethyl-O-(3,4-dihydro-4-oxo-1,2,3-benzotriazin-3-yl)uranium tetrafluoroborate) (38 mg, 0.109 mmol) was added directly to a stirred solution made from Amphotericin B Fmoc carbamate VI (125 mg, 0.109 mmol) (ref. 2), 8 mL of DMF and 30 μL of N,N-diisopropyl ethylamine.

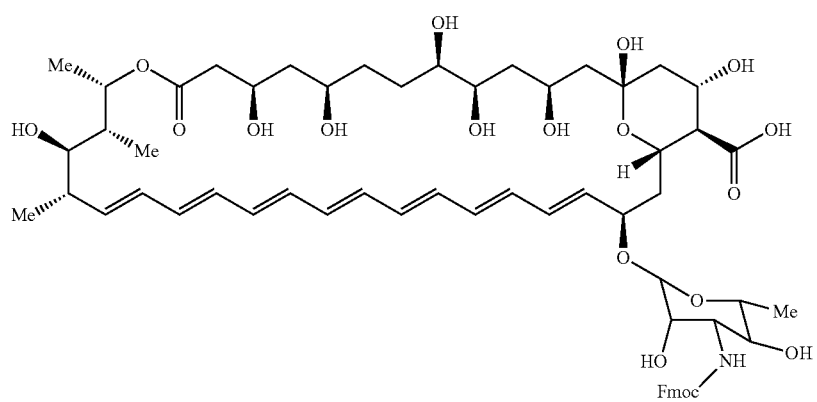

VI

The resulting mixture was stirred for 20 min at room temperature. After the reaction was completed (as judged by monitoring the formation of product by TLC, CHCl$_3$/MeOH/H$_2$O; 60/10/1, v/v/v, R$_f$ 0.50), the mixture was added, dropwise, into 200 mL of diethyl ether and the yellow precipitate collected by centrifugation. The resulting solid was further purified by column chromatography using silica gel using CHCl$_3$/MeOH/H$_2$O (60/10/1, v/v/v) as the eluent. The first major yellow band collected gave 121 mg (86%) of the title compound having $^1$H NMR (500 MHz, CD$_3$OD/CDCl$_3$, 1/5, 25° C., ppm): δ 8.37 (d, J=7.5 Hz, 1H), 8.17 (d, J=6.8 Hz, 1H), 7.90 (t, J=7.7 Hz, 1H), 7.76 (m, 3H), 7.63 7.47 (m, 2H), 7.40-7.18 (m, 4H), 6.69-5.93 (m, 14H), 5.60-5.21 (m, 2H), 4.96-4.18 (m, 6H), 3.94-3.57 (m, 5H), 3.46-3.21 (m, 5H), 2.76-2.06 (m, 5H), 2.04-1.25 (m, 17H), 1.22 (d, J=6.3 Hz, 3H), 1.13 (d, J=6.3 Hz, 3H), 1.03 (d, J=7.1 Hz, 3H). HR-ESI MS for C$_{64}$H$_{86}$N$_4$O$_{19}$[Na$^+$] Calcd: 1313.5728. Found: 1313.5752. The structure of N-Fmoc Amphotericin B carbamate, (3,4-dihydro-4-oxo-1,2,3-benzotriazin-3-yl) ester (VII) is shown below:

Synthesis of Compound (V)

A solution made from 2 mL of anhydrous DMF, 42.4 mg (39.7 μmol) of amine IV and 6.5 μL of triethylamine was added, dropwise, to a solution made from 52.7 mg (40.8 μmol) of N-Fmoc Amphotericin B carbamate, (3,4-dihydro-4-oxo-1,2,3-benzotriazin-3-yl) ester (VII) in 0.500 mL of anhydrous DMF. The resulting mixture was stirred in closed flask for 5 h and then added dropwise into 45 mL of cold diethyl ether. The resulting solid was separated and triturated four times with diethyl ether. The crude product was purified by preparative thin layer chromatography (SiO$_2$, CHCl$_3$/MeOH/H$_2$O, 80/20/2, v/v/v) to give 46.8 mg (54%) of conjugate V having Rf 0.68 and $^1$H-NMR (CD$_3$OD/CDCl$_3$, 10/1, ppm): 7.49-7.75 (m, 4H); 7.18-7.40 (m, 4H); 6.08-6.60 (m, 14H); 5.30-5.45 (m, 2H); 3.12-4.95 (m, 28H); 3.92 (s, 2H); 3.76 (s, 2H); 0.89-2.58 (m, 111H); 0.69 (s, 6H).

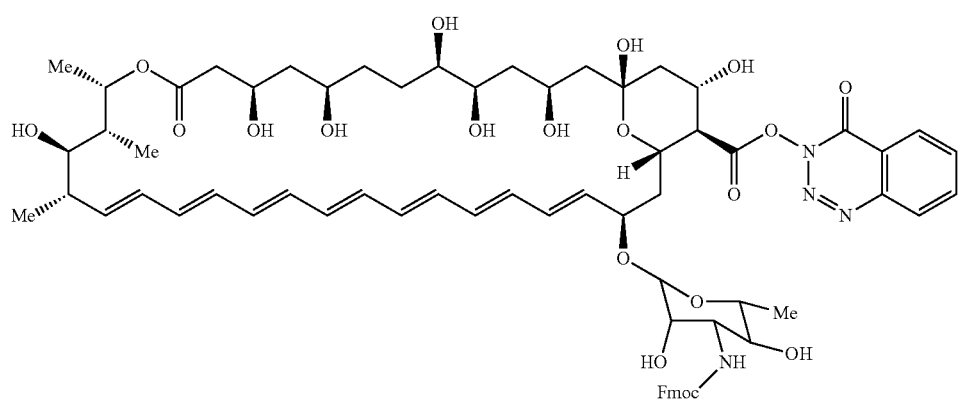

VII

Figure 5:
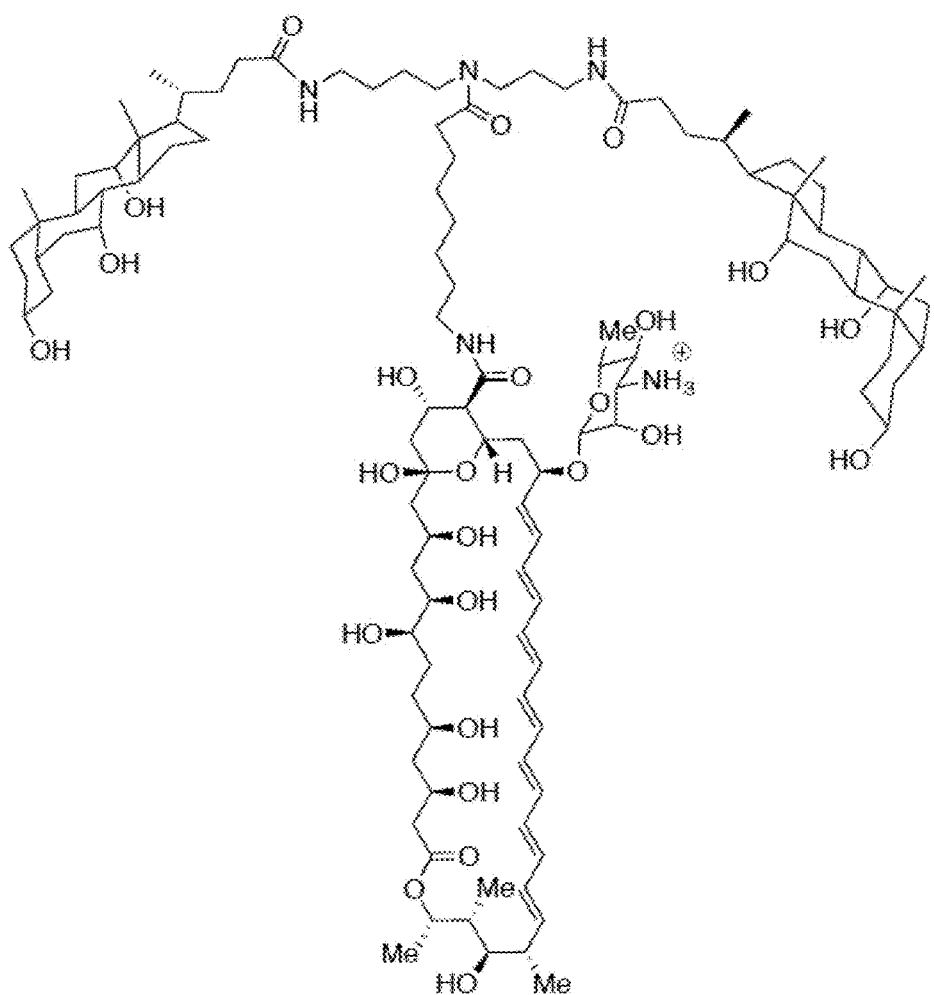
FIG. 5 shows a depiction of the chemical structure of VJ-1138.
Figure 6:
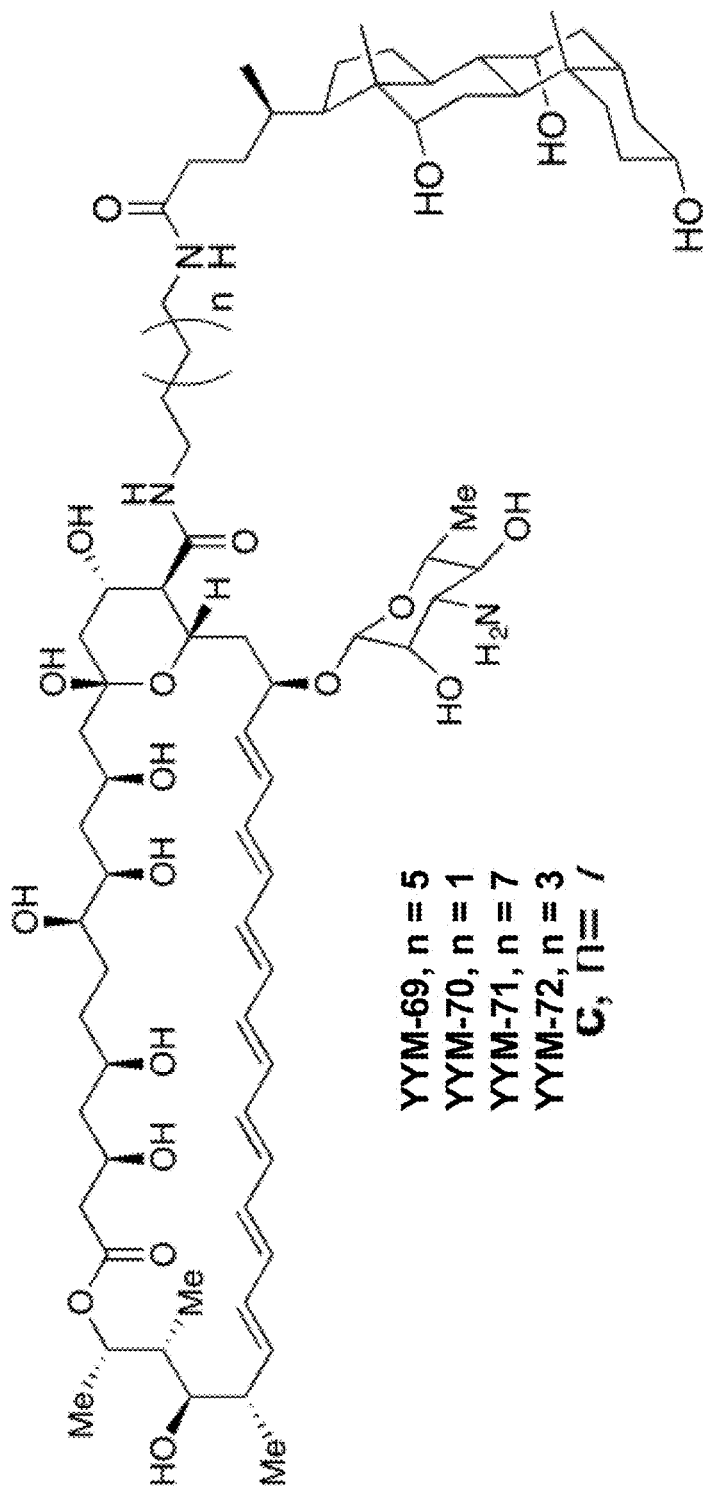
FIG. 6 shows a depiction of the chemical structure of certain single facial amphiphile conjugates.

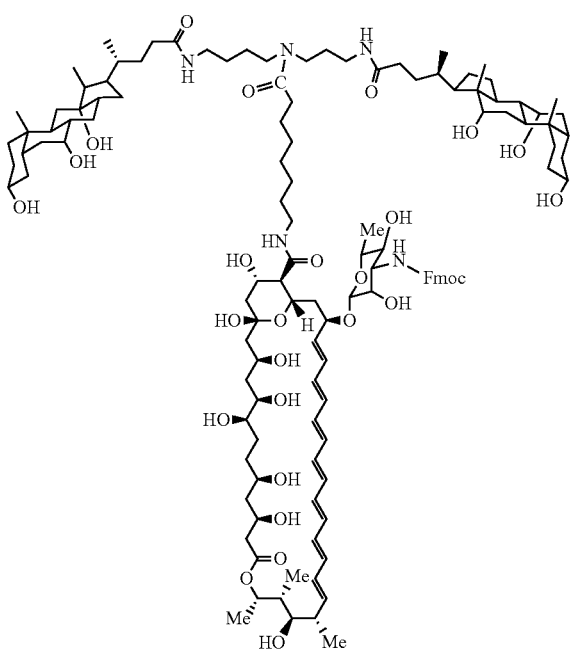

of diethyl ether and dried (1 Torr, rt, 16 h) to give 18.5 mg (97%) VJ-1138 having (CDCl$_3$/CD$_3$OD, 1/3, ppm): 6.08-6.60 (m, 14H); 5.30-5.45 (m, 2H); 3.12-4.95 (m, 25H); 3.92 (s, 2H); 3.76 (s, 2H); 0.89-2.58 (m, 111H); 0.69 (s, 6H). HR-ESI MS: for C$_{110}$H$_{182}$N$_5$O$_{25}$, (MH$^+$) calculated: 1973.3033; found: 1973.3063. The structure of VJ-1138 is shown on FIG. 5 and Table 2.

Synthesis of N$_1$,N$_3$-bis(N$_1$'N$_2$'-dicholeamido-lysyl)-N$_2$-(Boc-8-aminocapryloyl) spermidine amide
(VIII)

Synthesis of Amphotericin B conjugate VJ-1138

A solution was made from 21.2 mg (9.7 μmol) of compound V, 1.00 mL of DMF and 0.15 mL of piperidine and was stirred at 33° C. for 2 h. After this time, the solution was added to 10 mL of cold diethyl ether. The solid that was formed was separated and triturated four times with 10 mL To a solution made from 0.251 g (0.27 mmol) of N$_1$,N$_2$-lysine dicholeamide, 2.00 mL of anhydrous DMF, 51 μL (0.29 mmol) of N,N-diisopropylethylamine was added 0.1012 g (0.289 mmol) of TDBTU. After stirring the mixture for 15 min at rt in a closed flask, the solution of the activated ester was added to a solution made from 52.3 mg (0.135 mmol) of N$_2$-(Boc-8-aminocapryloyl)-spermidine amide (II) above, 0.60 mL of anhydrous DMF and 0.051 mL (0.29 mmol) of N,N-diisopropylethylamine. The resulting mixture was stirred for 24 h at rt and then added, dropwise, into 20 mL of 2% aqueous $NaHCO_3$. The precipitate formed was separated by centrifugation, washed three times with 20 mL of $H_2O$ and freeze dried to give 300 mg of crude product that was purified by gradient medium pressure chromatography (Isolera, SNAP Ultra 25 g, $CH_2Cl_2$/MeOH/$H_2O$, 85/15/1 to 80/20/2, v/v/v) to give 0.218 g (73%) of VIII having $R_f$ 0.69 ($CH_2Cl_2$/MeOH/$H_2O$, 80/20/2, v/v/v) and $^1$H-NMR ($CD_3OD$, ppm): 4.23 (m, 2H); 3.93 (s, 4H); 3.79 (s, 4H); 3.39 (m, 12H); 3.18 (m, 4H); 3.01 (m, 2H); 0.85-2.40 (m, 150H); 0.70 (s, 12H).

Synthesis of $N_1N_3$-bis($N_1'N_2'$-dicholeamido-lysyl)-$N_2$-(8-aminocapryloyl) spermidine amide (IX)

A solution was made from 65.4 mg (29.7 μmol) of $N_1,N_3$-bis(-$N_1'N_2'$-dicholeamido-lysyl)-$N_2$-(Boc-8-aminocapryloyl) spermidine amide (VIII), 2.5 mL of chloroform and 0.35 mL of trifluoroacetic acid, and the resulting solution stirred in closed flask for 2 h at rt. After that time, the solvents were removed under reduced pressure and the crude product (80.3 mg) was dissolved in 3.0 mL of methanol. To this solution was added 0.160 mL of 1 N aqueous NaOH and the solution stirred for 1.5 h at rt. The solvents were then removed under reduced pressure, and the product mixture dried (1 Torr, rt, 16 h). The resulting solid was triturated four times with 2 mL of $H_2O$ and dried (1 Torr, rt, 4 h) to give 58.5 mg (94%) of the free amine (IX) having $R_f$ 0.75, ($CHCl_3$/MeOH/$NH_4OH$, 70/30/6, v/v/v) and $^1$H-NMR ($CD_3OD$, ppm): 4.23 (m, 2H); 3.93 (s, 4H); 3.79 (s, 2H); 3.39 (m, 12H); 3.18 (m, 4H); 2.63 (m, 2H); 0.85-2.40 (m, 150H); 0.70 (s, 12H).

Synthesis of Conjugate X

A solution was made from 2 mL of anhydrous DMF, 58.3 mg (27.6 μmol) of amine (IX) and 4.5 μL (32 μmol) of triethylamine and the resulting solution was then added dropwise to a solution of 37.2 mg (28.8 μmol) of N-Fmoc Amphotericin B carbamate, (3,4-dihydro-4-oxo-1,2,3-benzotriazin-3-yl) ester (VII) in 0.500 mL of anhydrous DMF.

After stirring the mixture in a closed flask for 6 h at 34° C., it was then added dropwise into 25 mL of cold diethyl ether.

The precipitate formed was separated and triturated four times with 20 mL of diethyl ether. The crude product (75 mg) was purified by column chromatography and by preparative thin layer chromatography ($SiO_2$, $CHCl_3$/MeOH/$H_2O$, 80/25/3, v/v/v) to give 29.1 mg (28%) of conjugate X having Rf 0.68 $CHCl_3$/MeOH/$H_2O$, 80/25/3 (v/v/v) and $^1$H-NMR ($CDCl_3$/$CD_3OD$, 1/3, ppm): 7.50-7.78 (m, 4H); 7.20-7.41 (m, 4H); 6.08-6.60 (m, 14H); 5.30-5.45 (m, 2H); 3.12-4.95 (m, 35H); 3.92 (s, 4H); 3.76 (s, 4H); 0.89-2.58 (m, 175H); 0.69 (s, 12H).

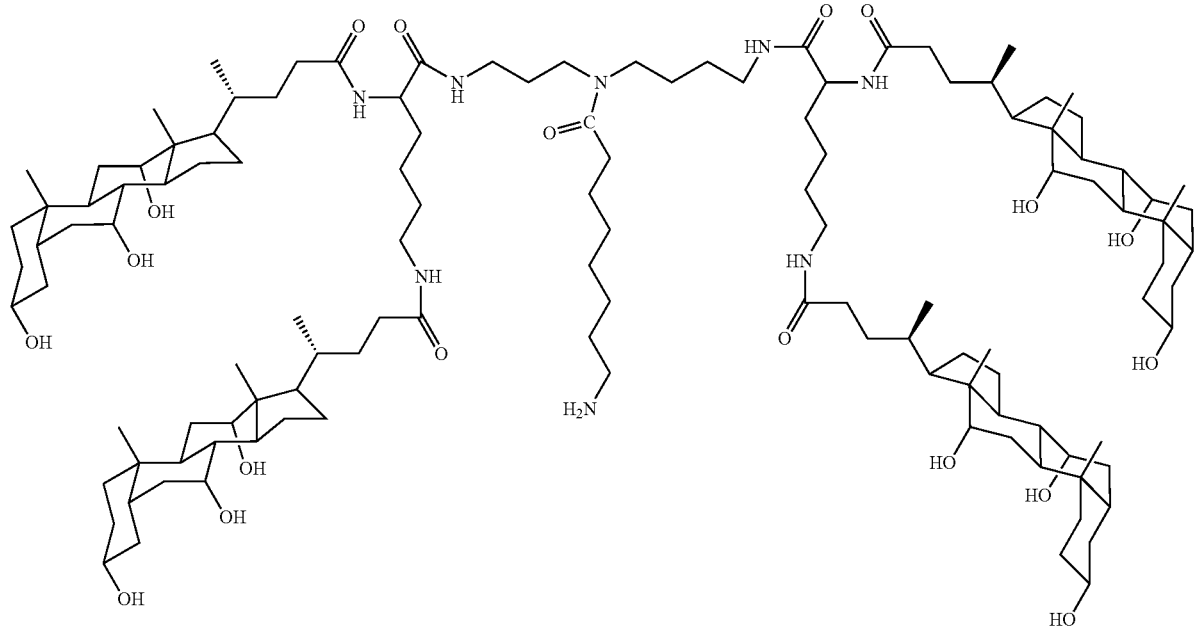

IX

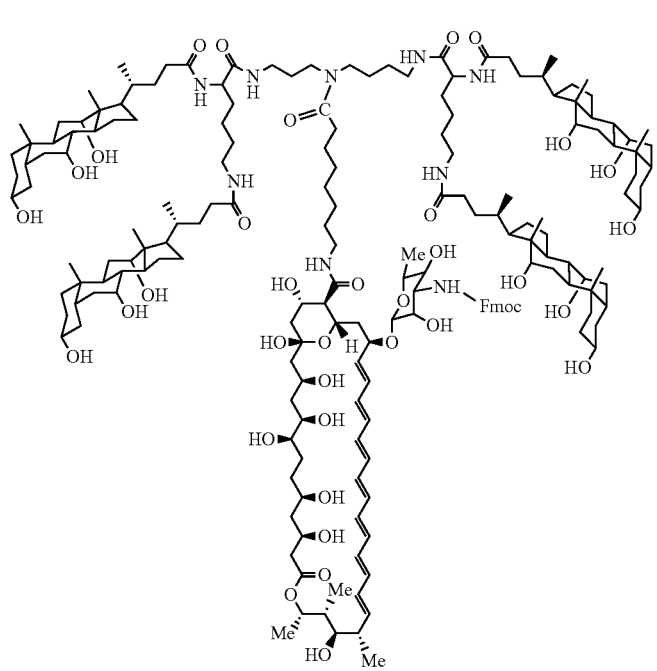

Synthesis of Conjugate 2a (VJ-1155)

A solution was made from 29.1 mg (9.0 μmol) of conjugate (X) (9.0 μmol), 0.80 mL of DMF and 0.080 mL of piperidine, and stirred for 7 h at 33° C. The solution was then added, dropwise, to 10 mL of cold diethyl ether. The solid that was formed was separated and triturated four times with 10 mL of diethyl ether and dried (1 Torr rt, 16 h) to give 25.7 mg (95%) of (2a) having $^1$H-NMR (CDCl$_3$/CD$_3$OD, 1/3, ppm): 6.08-6.60 (m, 14H); 5.30-5.45 (m, 2H); 3.12-4.95 (m, 32H); 3.92 (s, 4H); 3.76 (s, 4H); 0.89-2.58 (m, 175H); 0.69 (s, 12H). HR-ESI MS: for $C_{170}H_{281}N_9O_{35}$, (M+2Na) calculated: 1527.5135; found: 1527.5197.

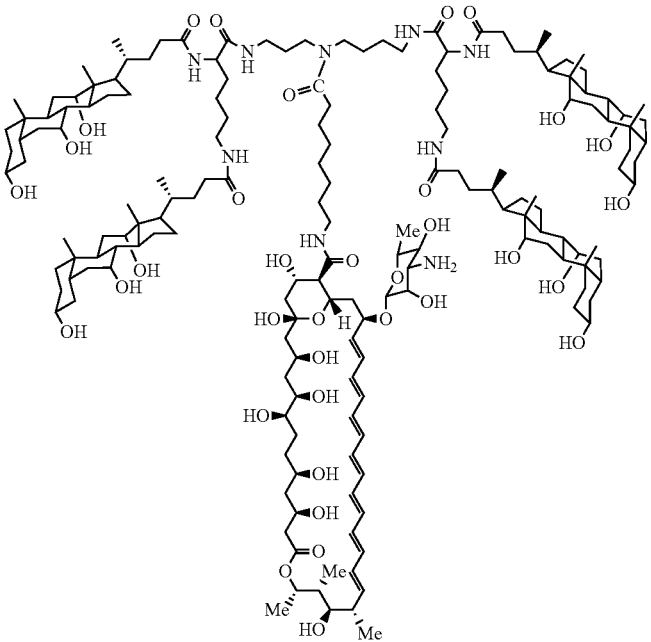

Critical Aggregation Concentration, Hemolytic Activity and Cytotoxicity Measurements:

Determination of Critical Aggregation Concentration (CAC) of AmphB and molecular conjugates. Solutions of AmphB and molecular conjugates in DMSO (Sigma-Aldrich) were prepared having a concentration of 1.00 mM. Aliquots (1-10 μL) were then introduced into test tubes containing 0.750 mL to 5.88 mL of phosphate-buffered saline (PBS), pH 7.4 at 37° C. to give concentrations ranging from 0.17 to 13.1 μM. After vortex mixing for 10 seconds, the solution was transferred to a 1.60 mL UV cuvette that was maintained at 37° C. The UV spectrum was then recorded in the range of 250-550 nm. The absorbance at 408 nm was plotted as a function of the reciprocal value of the concentration of AmB and the critical aggregation concentration of the molecular conjugates was then determined, graphically.

Hemolysis Measurements:

Sheep Red Blood Cells, 10%, in saline (Innovative Research, Novi, Mich.), were diluted in saline (pH 7.4) to a concentration of 4%, which corresponds to $4 \times 10^7$ cells/mL. All measurements were carried out in duplicate. Solutions of Amphotericin B (Sigma-Aldrich) were prepared by adding 10 μL of a DMSO solution containing a given concentration of the antibiotic (i.e., ranging from 0.2 mM to 50 mM) to 490 μL of PBS. After the resulting solution was vortex mixed for 30 seconds (s) it was incubated at 37° C. for 15 min. The resulting solution of antibiotic (500 μL) was then mixed with 500 μL of the 4% erythrocyte dispersion at 37° C. in a 1 mL plastic centrifuge vial to give a dispersion that was vortex mixed at slow rate for 5 s. After 1 h of incubation at 37° C., all samples were centrifuged (1500 g, Eppendorf centrifuge 5415C, 5000 rpm) at rt for 5 min. The supernatant (~0.7 mL) from each plastic vial was carefully separated from sediment using a disposable glass pipette and quickly transferred to test tube. A volume of 50 μL of this supernatant was then transferred to a UV cell containing 500 μL of PBS that was maintained at 37° C. The UV spectrum was then scanned (450-650 nm) and the absorbance at 575 nm used to determine the extent of hemolysis. The extent of 0% and 100% of hemolysis was obtained from A575 values of experiments that were run in absence of AmphB (control, $[A_{575},]_o$) and in presence, 100 μM AmphB ($[A_{575}]max$), respectively. The concentrations of AmphB and the molecular conjugate that resulted in 50% release of hemoglobin, $\{[A_{575}]max-[A_{575}]_o\}/2$, which are our $EH_{50}$ values, were determined graphically.

Cell Culture of Human Embryonic Kidney HEK293:

Human embryonic kidney HEK293 cells were cultured in Dulbecco's modified Eagle's medium (DMEM supplemented with 10% FBS, 100 U/mL penicillin, and 0.1 mg/mL SI-10 streptomycin) in a humidified atmosphere of 5% $CO_2$ at 37° C.

Inhibition of Cell Growth:

HEK293T cells were seeded in 96-well plates at a density of 6,000 cells/well and incubated overnight. Before treatment, compounds aliquots were solubilized in DMSO to obtain 10 mM stock solutions. Appropriate volumes of these stock solutions were added to DMEM media so the final concentration of DMSO is equal to 1%. After removal of cell media, 50 μL of treatment solutions were added to each well and incubated at 37° C. for 2 h. After treatment, the media was removed, and 100 μL of complete medium was added to each well before returning the plate to the incubator. Cell viability was determined after 72 h using the colorimetric MTT assay. Briefly, 10 μL of a 5 mg/mL MTT stock solution was added to the treated cells and incubated for 2 h at 37° C. The resulting formazan crystals were solubilized in 200 μL of DMSO, and the absorbance was measured at 580 nm using an Infinite 200 PRO microplate reader (Tecan). Cell viability was calculated against control cells treated with the vehicle in DMEM.

Determination of MIC and MFC Values:

Minimum inhibitory concentrations (MIC) and minimum fungicidal concentrations (MFC) are the lowest concentrations that are required for completely inhibiting growth, and killing at least 99% of the fungi, respectively.

Example 3: Alternative Synthetic Route for Generation of Key Intermediates of Anti-Microbial Conjugates As depicted in Scheme 2 below, an alternative synthesis strategy for the key intermediate, $N_1,N_3$-dicholeamido-$N_2$-(8-N-Boc-aminocapryloyl) spermidine triamide, is developed. This synthetic strategy allows cholic acid to be converted to a key intermediate in 3 steps with an overall yield of 65%. Subsequent coupling with an activated and protected form of AmphB, followed by deprotection (2 steps) gives an isolated yield of 52%. The activated and protected form of AmphB can be formed from AmphB in 2 steps with an isolated yield of 71%.

Scheme 2:

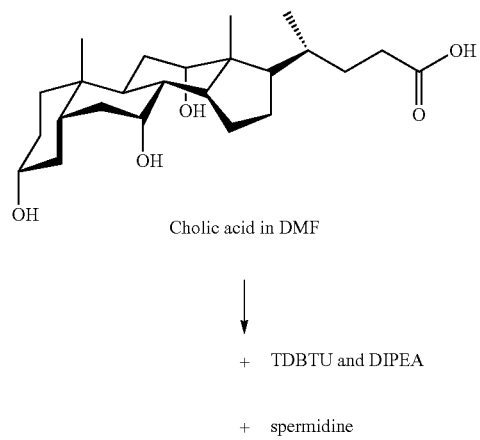

Cholic acid in DMF

↓

+ TDBTU and DIPEA

+ spermidine

-continued
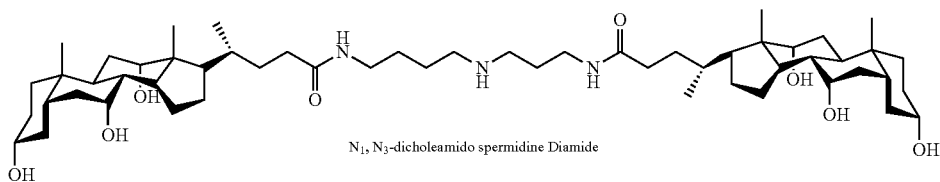
N₁, N₃-dicholeamido spermidine Diamide
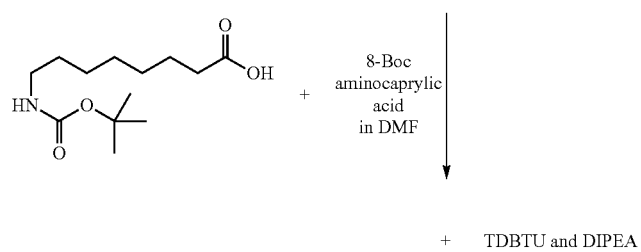
8-Boc aminocaprylic acid in DMF
+ TDBTU and DIPEA
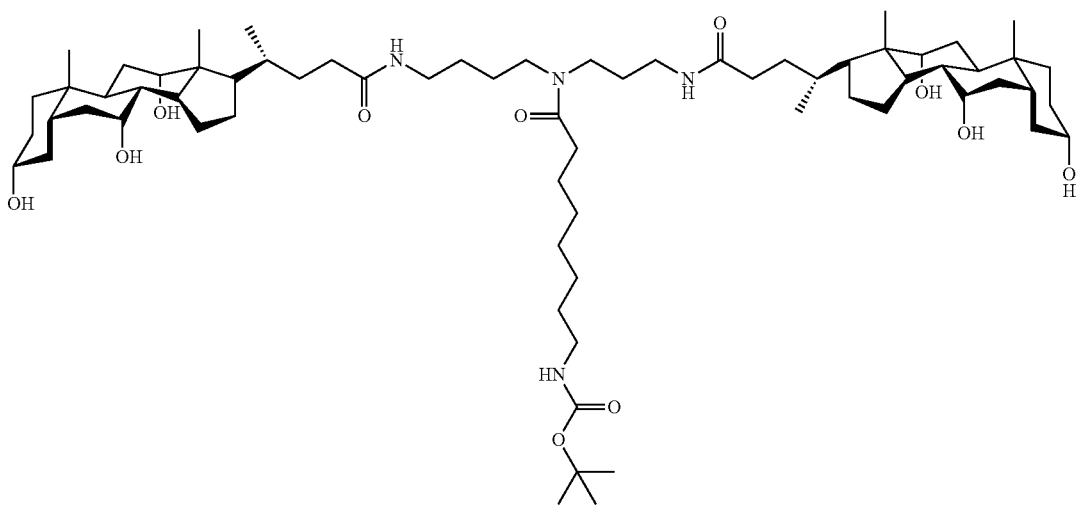
N₁, N₃-dicholeamido-N₂-(8-N-Boc-aminocapryloyl) spermidine triamide
+ TFA for removal of Boc protecting group

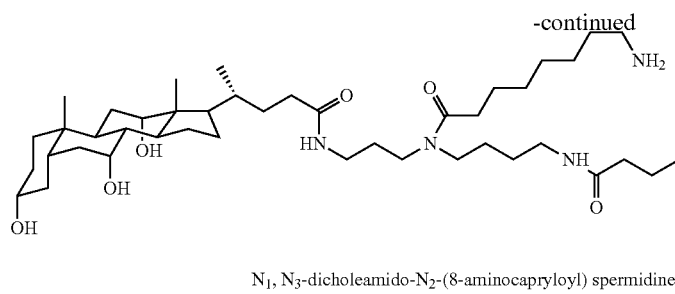

$N_1$, $N_3$-dicholeamido-$N_2$-(8-aminocapryloyl) spermidine

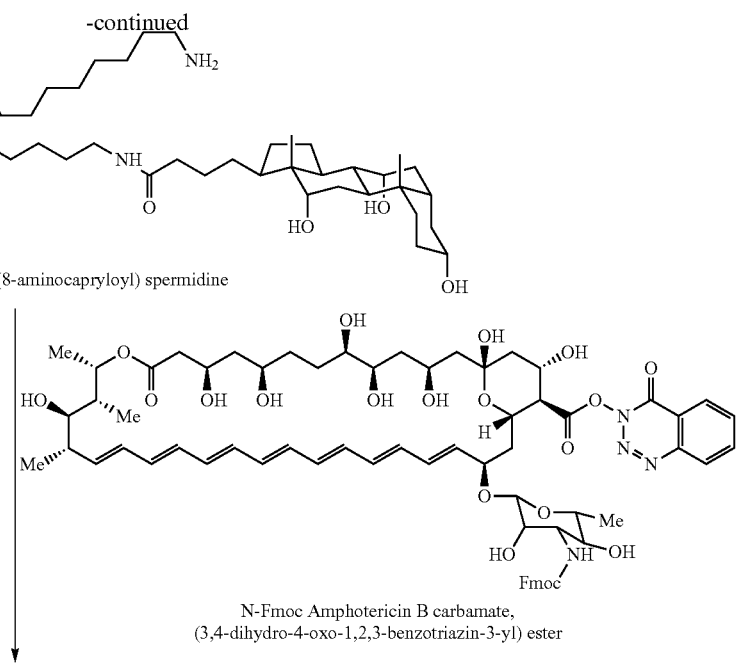

N-Fmoc Amphotericin B carbamate,
(3,4-dihydro-4-oxo-1,2,3-benzotriazin-3-yl) ester

Synthesis of $N_1$,$N_3$-dicholeamido spermidine diamide

A stirred solution of 163.43 mg (0.4 mmol) cholic acid in 5 ml DMF was prepared. To this was added 139.64 mg (0.4 mmol) TDBTU (N,N,N',N'-Tetramethyl-O-(3,4-dihydro-4-oxo-1,2,3-benzotriazin-3-yl)uronium tetrafluoroborate) and 100 μL DIPEA (N,N-Diisopropylethylamine). The mixture was stirred at room temperature for 10 minutes. Then 29.05 mg (0.2 mmol) spermidine was added into the reaction mixture and stirred 4 hours at room temperature. After the reaction completed (monitored by TLC), the mixture was dropped into 200 mL 5% NaHCO$_3$, and the precipitates collected by centrifugation. The solid was further purified by chromatography using CHCl$_3$:MeOH:NH$_4$OH=60:10:1 to CHCl$_3$:MeOH:NH$_4$OH=60:20:3 as eluent, collecting the second major band and removing the solvent under reduced pressure, to afford 131 mg of product at a yield of 71%.

Synthesis of $N_1$,$N_3$-dicholeamido-$N_2$-(8-N-Boc-aminocapryloyl) spermidine triamide 34.91 mg (0.1 mmol) TDBTU (N,N,N',N'-Tetramethyl-O-(3,4-dihydro-4-oxo-1,2,3-benzotriazin-3-yl)uronium tetrafluoroborate) and 60 μL DIPEA (N,N-Diisopropylethylamine) was added into stirring solution of 25.93 mg (0.1 mmol), 8-Boc aminocaprylic acid in 3 mL DMF. The mixture was stirred at room temperature for 10 minutes. Then 101.83 mg (0.11 mmol) $N_1$,$N_3$-dicholeamido spermidine diamide was added into the reaction mixture and continuously stirred for 4 hours at room temperature. After the reaction completed (monitored by TLC, $R_f$=0.65), the mixture was dropped into 200 mL 5% NaHCO$_3$, and the precipitates collected by filtration. The solid was further purified by chromatography using CHCl$_3$:MeOH:H$_2$O=60:10:1 as eluent, afforded 106 mg product, yield 91%.

The $N_1$,$N_3$-dicholeamido-$N_2$-(Boc-8-aminocapryloyl) spermidine triamide was mixed in solution with chloroform and trifluoroacetic acid and stirred in closed flask for 2 h at rt to remove the Boc. The solvents were removed under reduced pressure affording a crude product. This product was then dissolved in methanol. To this methanolic solution was then added 1N aqueous NaOH and the solution stirred at rt for 1 h. The solvents were then removed under reduced pressure, and the crude product dried (1 Torr, rt, 16 h). The resulting solid was triturated four times using 10 mL of H$_2$O and dried (1 Torr rt, 4 h) to give the free amine for subsequent combination with N-Fmoc Amphotericin B carbamate, (3,4-dihydro-4-oxo-1,2,3-benzotriazin-3-yl) ester as described in relation to Scheme 1.

Example 4: Toxicity Taming Using Single Facial Amphiphile Conjugates

An effort was under taken to generate and test simpler conjugates of membrane disruptive drugs using AmphB as an example. Essentially, a single wall facial amphiphile (e.g., a choloyl moiety) is covalently attached to the drug to serve as a "float." This float is intended to keep the agent close to the membrane surface most of the time. While the membrane-disrupting action of the drug should still be operative, deep penetration of aggregated forms into mammalian membranes (thought to be necessary for membrane rupture) would be prevented. It should be noted that this strategy is distinctive from the embodiments of molecular umbrellas described herein. In the simple taming strategy, only a single facial amphiphile is added thus greatly simplifying chemical synthesis.

In essence, single facial amphiphile-active agent conjugates are composed of one facial amphiphiles (FA) that is attached to the active agent (D) via a linker L according to the general formula (II):

(II)

wherein FA is a sterol moiety that has the property of being a facial amphiphile; and wherein L is a linker connecting Y to active agent D, wherein L is a diamine containing from about 3 to about 15 carbon groups (n) separating the amine groups of the diamine. In certain embodiments, L is selected from a butanediamine, hexanediamine, octanediamine and decanediamine.

In certain embodiments, a facially amphiphilic bile acid (e.g., cholic acid, deoxycholic acid, chenodeoxycholic acid, or lithocholic acid) or derivative thereof is selected for constructing a suitable facially amphiphilic framework.

To test the approach, three derivatives of Amphotericin B were synthesized and tested as prototypes; i.e., 1a, 1b and 1c (Scheme 3). Each conjugate was prepared by condensing an activated and protected form of AmphB (2) with the corresponding α,ω-diamine that had been monoacylated with cholic acid (3).

Synthetic Procedures

Synthesis of $N_1$-cholyl-1,4-butanediamine 3a (N,N,N',N'-Tetramethyl-O-(3,4-dihydro-4-oxo-1,2,3-benzotriazin-3-yl)uranium tetrafluoroborate) (210 mg, 0.6 mmol) was added directly to a stirred solution that was made from cholic acid (245 mg, 0.6 mmol), 8 mL of DMF and 400 μL of N,N-diisopropylethylamine. The resulting mixture was stirred for 20 min at room temperature. Then Fmoc-1,4-diaminobutane (CHEM-IMPEX INT'L INC.) (208 mg, 0.53 mmol) was added and stirring continued for 4 h. After the reaction was completed (monitored by TLC, ($CHCl_3$/MeOH/$H_2O$, 60/10/1, v/v/v, Rf 0.60), the product mixture was added, dropwise, into 200 mL of 5% $NaHCO_3$ and the precipitate collected by filtration, and washed 3 times with de-ionized water. The resulting solid was further purified by column chromatography using silica gel and $CHCl_3$/MeOH/

Scheme 3:

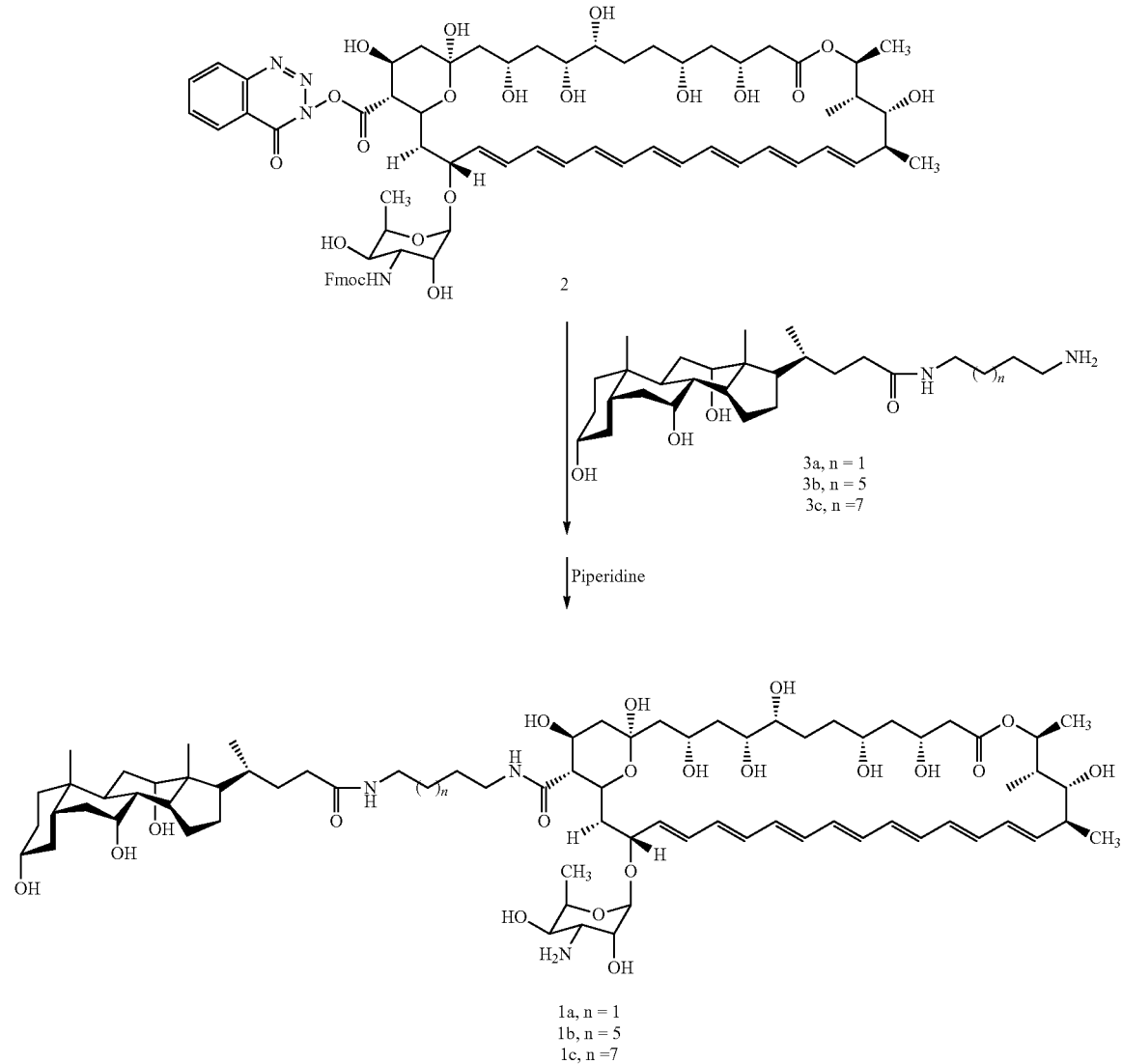

$H_2O$ (60/10/1, $R_f$=0.60, v/v/v) as the eluent to give 360 mg (97%) of the Fmoc-protected intermediate.

This intermediate was dissolved in 4 mL DMF and 2 mL piperidine and the mixture stirred for 20 min. After the reaction was completed, the mixture was added dropwise into 200 mL diethyl ether and the precipitate collected by filtration. The product proved to be pure enough for subsequent coupling and was used directly, without further purification. $^1$H NMR (500 MHz, MeOD) δ 3.96 (s, 1H), 3.80 (s, 1H), 3.44-3.34 (m, 1H), 3.22-3.13 (m, 2H), 2.66 (t, J=6.9 Hz, 2H), 2.45-0.95 (m, 31H), 0.94 (d, J=17.7 Hz, 3H), 0.72 (s, 3H).

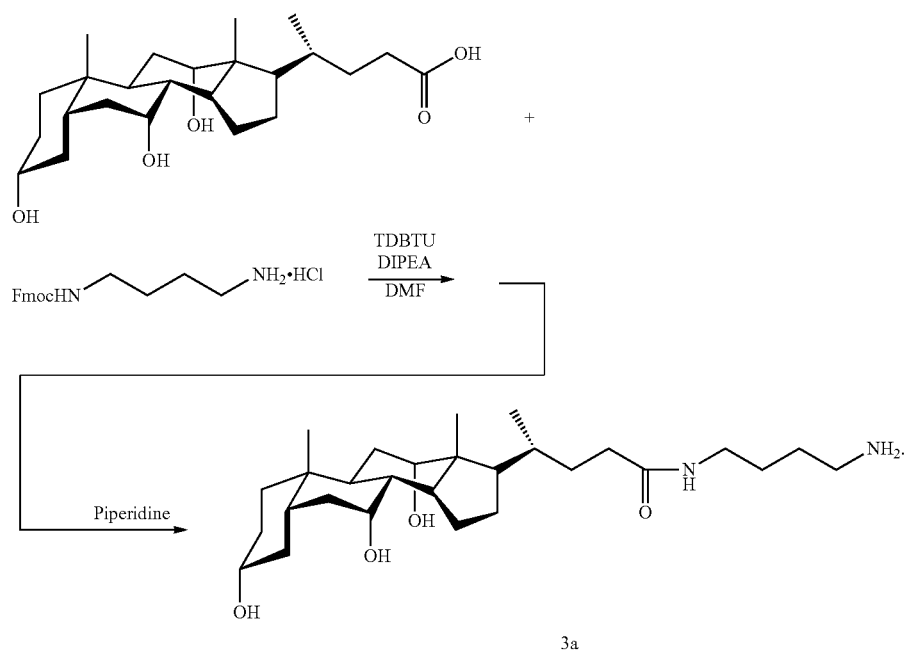

3a

Synthesis of $N_1$-cholyl-1,8-octanediamine 3b (N,N,N',N'-Tetramethyl-O-(3,4-dihydro-4-oxo-1,2,3-benzotriazin-3-yl)uranium tetrafluoroborate) (180 mg, 0.52 mmol) was added directly to a stirred solution that was made from cholic acid (215 mg, 0.52 mmol), 8 mL of DMF, 4 ml of $CHCl_3$ and 300 μL of N,N-diisopropylethylamine. After stirring the resulting mixture for 20 min at room temperature, it was added dropwise into solution made from 1,8-octanediamine (750 mg, 5.2 mmol), 5 mL of DMF and 5 mL of $CHCl_3$. The reaction mixture was stirred at room temperature for an additional 4 h. After the reaction was completed [as judged by monitoring the formation of product by TLC ($CHCl_3$/MeOH/$H_2O$; 60/10/1, v/v/v)], the product mixture was added, dropwise, into 200 mL of 5% $NaHCO_3$ and the precipitate collected by filtration. The solid was then washed 3 times with de-ionized water and further purified by column chromatography using $CHCl_3$/MeOH/$H_2O$ (40/10/1, v/v/v) to $CHCl_3$/MeOH/$NH_4OH$ (40/10/1, $R_f$=0.55, v/v/v) as the eluent to give 276 mg (98%) of 3b having $^1$H NMR (500 MHz, MeOD) δ 3.96 (s, 1H), 3.81 (s, 1H), 3.44-3.35 (m, 1H), 3.23-3.10 (m, 2H), 2.73-2.57 (m, 2H), 2.37-0.98 (m, 39H), 0.92 (s, 3H), 0.72 (s, 3H).

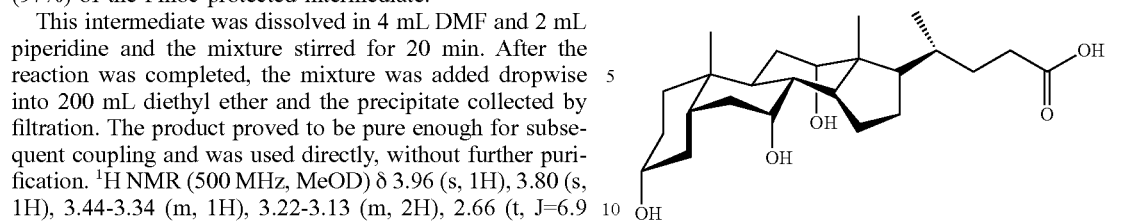

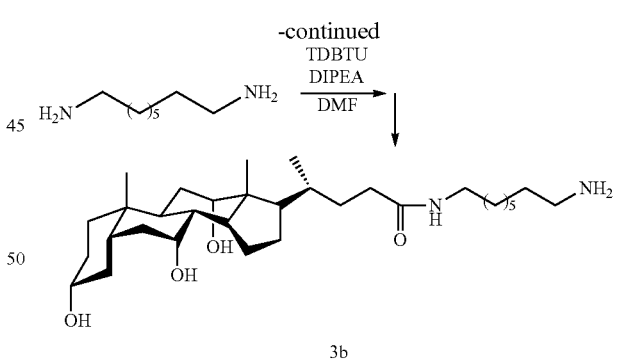

3b

Synthesis of $N_1$-cholyl-1,10-decanediamine 3c (N,N,N',N'-Tetramethyl-O-(3,4-dihydro-4-oxo-1,2,3-benzotriazin-3-yl)uranium tetrafluoroborate) (215 mg, 0.52 mmol) is added directly to a stirred solution that is made from cholic acid (215 mg, 0.52 mmol), 8 mL of DMF and 200 μL, of N,N-diisopropylethylamine. The resulting mixture is stirred for 20 min at room temperature. Then 1,10-decanediamine (900 mg, 5.2 mmol) is added and stirring continued for an additional 4 h. After the reaction is completed [as judged by monitoring the formation of product by TLC (CHCl$_3$/MeOH/H$_2$O; 60/10/1, v/v/v)], the mixture is added, dropwise, into 200 mL of 5% NaHCO$_3$ that is maintained at 60° C., and the precipitate collected by filtration. The solid was then washed 3 times with de-ionized water. The resulting solid is further purified by column chromatography using silica gel using CHCl$_3$/MeOH/H$_2$O (40/10/1, v/v/v) to CHCl$_3$/MeOH/NH$_4$OH (50/10/1, Rf=0.45, v/v/v) as the eluent to give 285 mg (yield: 96%) of 3c having $^1$H NMR (500 MHz, MeOD) δ 3.96 (s, 1H), 3.80 (s, 1H), 3.36 (d, J=11.2 Hz, 1H), 3.24-3.04 (m, 2H), 2.80-2.57 (m, 2H), 2.43-0.96 (m, 43H), 0.92 (s, 3H), 0.72 (s, 3H).

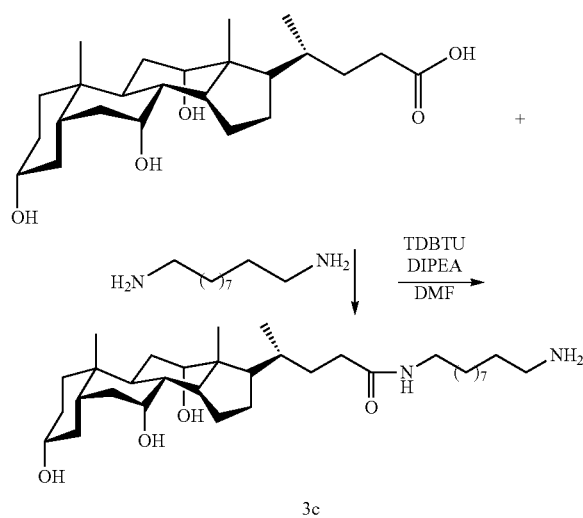

Amphotericin B Conjugate 1a.

To a solution that was made from N-Fmoc Amhotericin B carbamate-(3,4-dihydro-4-oxo-1,2,3-benzotriazin-3-yl) ester (2) (of Scheme 3) 30 mg (23 μmol), 12.0 mg (25 μmol) of amine (3a) (of Scheme 3) and 2 mL of anhydrous DMF was added 50 μL of N,N-diisopropylethylamine. The resulting mixture was stirred in closed flask for 5 h at room temperature. After the starting material (2) completely disappeared (monitored by TLC, CHCl$_3$/MeOH/H$_2$O, 50/10/1, v/v/v), 0.5 mL of piperidine was added and the mixture allowed to stir for an additional 15 min. This mixture was then added dropwise into 100 mL of cold diethyl ether. The resulting solid was collected by centrifugation and the crude product purified by flash chromatography using (CHCl$_3$/MeOH/H$_2$O, 60/20/3, v/v/v) as eluent. The product was further purified by preparative thin layer chromatography (CHCl$_3$/MeOH/H$_2$O, 10/5/1, v/v/v) to give 26 mg (80%) of conjugate 1a (a.k.a. YYM-70) (Rf 0.78) having $^1$H-NMR (500 MHz, CD$_3$OD:CHCl$_3$=2:1, ppm): δ 6.62-5.89 (m, 12H), 5.42-5.32 (m, 2H), 4.56-4.36 (m, 3H), 4.29-4.13 (m, 2H), 3.95 (s, 1H), 3.87-3.77 (m, 2H), 3.73 (t, J=10.7 Hz, 1H), 3.64 (d, J=12.8 Hz, 1H), 3.40-3.32 (s, 1H), 3.29-3.07 (m, 8H), 2.57-0.94 (m, 65H), 0.91 (s, 3H), 0.71 (s, 3H).

Amphotericin B Conjugate 1b.

To a solution that was made from N-Fmoc Amhotericin B carbamate-(3,4-dihydro-4-oxo-1,2,3-benzotriazin-3-yl) ester (2) (of Scheme 3) 25.8 mg (20 μmol), 22 mg (40 μmol) of amine 3b (of Scheme 3) and 2 mL of anhydrous DMF was added 50 μL of N,N-diisopropylethylamine. The resulting mixture was stirred in closed flask for 5 h. After the starting material (2) completely disappeared (monitored by TLC, CHCl$_3$/MeOH/H$_2$O, 50/10/1, v/v/v), 0.5 mL of piperidine was added and the mixture continue stirred for an additional 15 min. The product mixture was then added dropwise into 100 mL of cold diethyl ether. The resulting solid was collected by centrifugation and the crude product purified by flash chromatography using (CHCl$_3$/MeOH/H$_2$O, 60/20/3, v/v/v) as eluent. The product was further purified by preparative thin layer chromatography (CHCl$_3$/MeOH/H$_2$O, 12/5/1, v/v/v) to give 21.6 mg (75%) of conjugate 1b (a.k.a. YYM-69) (Rf 0.72) having $^1$H-NMR (500 MHz, CD$_3$OD: CHCl$_3$=2:1, ppm): δ 6.59-5.94 (m, 12H), 5.53-5.22 (m, 2H), 4.56-4.34 (m, 3H), 4.31-4.21 (m, 1H), 4.17 (t, J=9.9 Hz, 1H), 3.95 (s, 1H), 3.82 (dd, J=20.3, 2.1 Hz, 2H), 3.73 (t, J=9.5 Hz, 1H), 3.64 (d, J=9.9 Hz, 1H), 3.45-3.31 (m, 1H), 3.27-3.01 (m, 8H), 2.72-0.93 (m, 73H), 0.91 (s, 3H), 0.70 (s, 3H).

Amphotericin B Conjugate 1c.

To a solution that was made from N-Fmoc Amhotericin B carbamate, (3,4-dihydro-4-oxo-1,2,3-benzotriazin-3-yl) ester (2) (of Scheme 3) 30 mg (23 μmol), 20 mg (35 μmol) of amine 3c (of Scheme 3) and 2 mL of anhydrous DMF was added 50 μL of N,N-diisopropylethylamine. The resulting mixture was stirred in closed flask for 5 h. After the starting material (2) completely disappeared (monitored by TLC, CHCl$_3$/MeOH/H$_2$O, 50/10/1, v/v/v), 0.5 mL of piperidine was added and the mixture stirred for an additional 15 min. The product mixture was added dropwise into 100 mL of cold diethyl ether. The resulting solid was collected by centrifugation and the crude product purified by flash chromatography using (CHCl$_3$/MeOH/H$_2$O, 40/10/1, v/v/v) as eluent. The product was further purified by preparative thin layer chromatography (CHCl$_3$/MeOH/H$_2$O, 60/20/3, v/v/v) to give 24.2 mg (71%) of conjugate 1c (a.k.a. YYM-71) (Rf 0.6) having $^1$H-NMR (500 MHz, CD$_3$OD:CHCl$_3$=2:1, ppm): δ 6.55-5.94 (m, 12H), 5.52-5.14 (m, 2H), 4.55-4.27 (m, 3H), 4.22 (td, J=10.9, 4.7 Hz, 1H), 4.13 (t, J=10.1 Hz, 1H), 3.94 (s, 1H), 3.86-3.77 (m, 1H), 3.72 (t, J=9.9 Hz, 1H), 3.62 (d, J=10.7 Hz, 1H), 3.45-3.34 (m, 1H), 3.26-3.01 (m, 8H), 2.63-0.91 (m, 77H), 0.89 (s, 3H), 0.68 (s, 3H).

A further Amphothericin B conjugate, YYM-72, was also made wherein in the diamine linker of Scheme 3, n=3.

In the resulting molecules shown above, the AmB moiety is free to extract ergosterol to the membrane surface of fungal cells via a "sponge" mechanism to form lethal pores. However, the float restricts deep penetration of aggregated forms into mammalian membranes.

The above molecules were tested for antifungal activity. Minimum inhibitory concentrations (MIC) and minimum fungicidal concentrations (MFC) are the lowest concentrations that are required for completely inhibiting growth, and killing at least 99% of the fungi, respectively. As is apparent from Table 4 below, there is a general trend; i.e., increased antifungal activity is observed as the length of the hydrocarbon chain that separates the facial amphiphile from the Amphotericin B moiety is decreased.

TABLE 4

| Antifungal activities | | | | |
|---|---|---|---|---|
| | MIC/MFC (μg/mL) | | | |
| Microbe | AmB | 1a (YYM-70) | 1b (YYM-69) | 1c (YYM-71) |
| C. albicans | 0.5/1 | 1/1 | 2/2 | >16/— |
| C. glabrata | 0.5/1 | 2/2 | >16/— | >16/— |
| C. neoformans | 0.3/0.5 | 1/2 | 1/2 | 2/>16 |
| C. gatti | 0.3/0.5 | 1/2 | 1/2 | 1>16/ |

Figure 7:
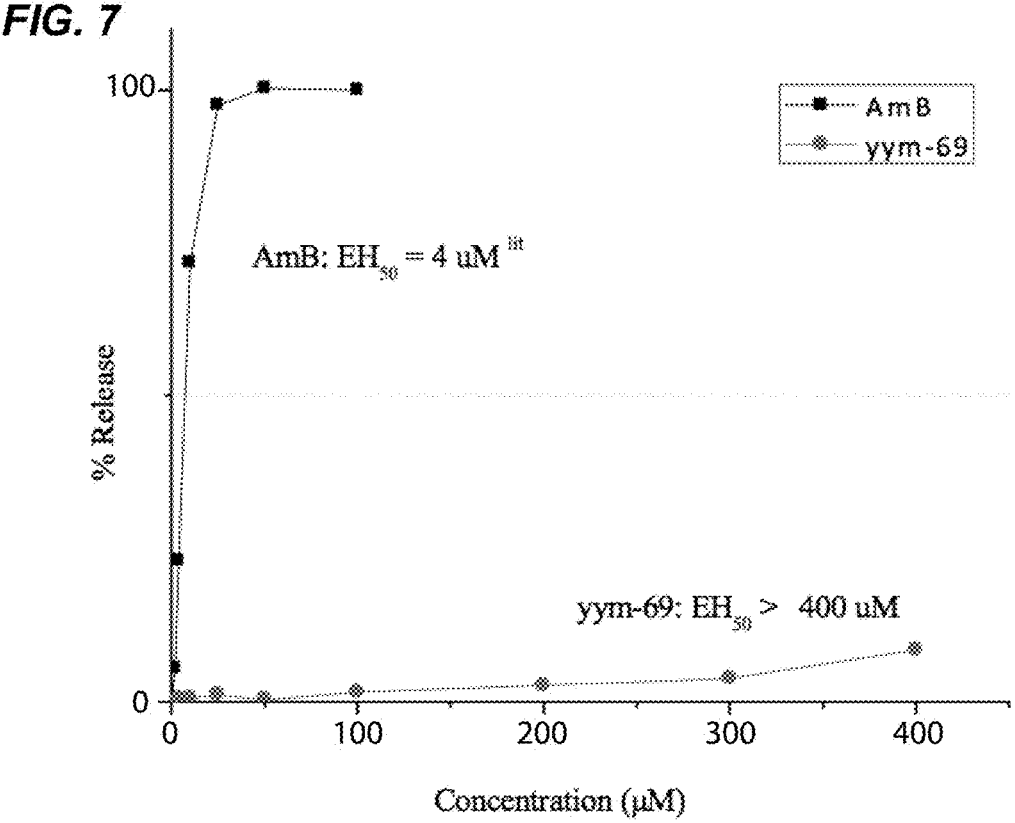
FIG. 7 compares the hemolytic activity of AmphB versus conjugate YYM-69 at various concentrations.
Figure 8:
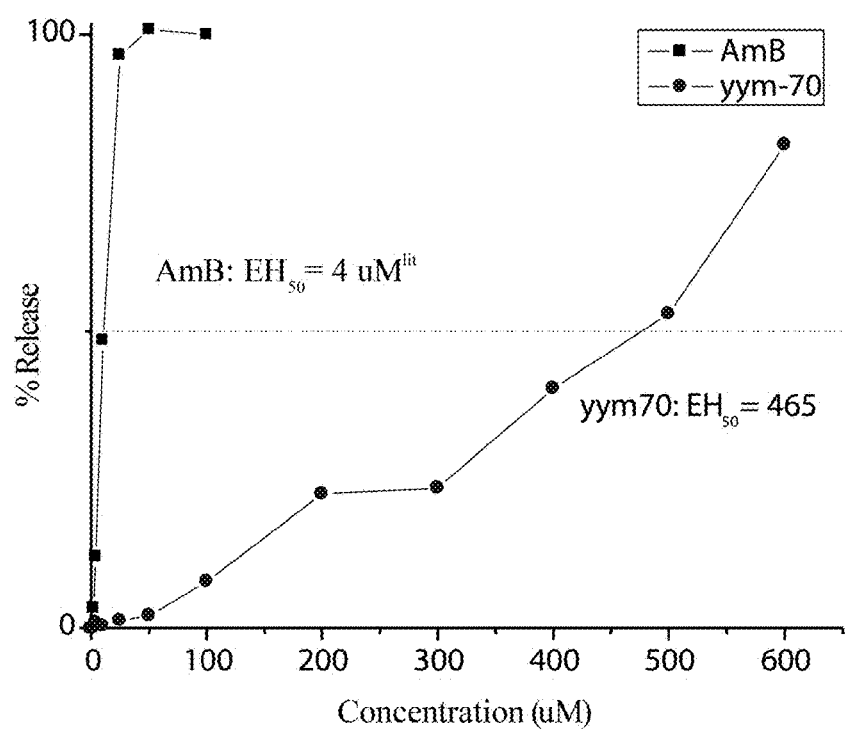
FIG. 8 compares the hemolytic activity of AmphB versus conjugate YYM-70 at various concentrations.
Figure 9:
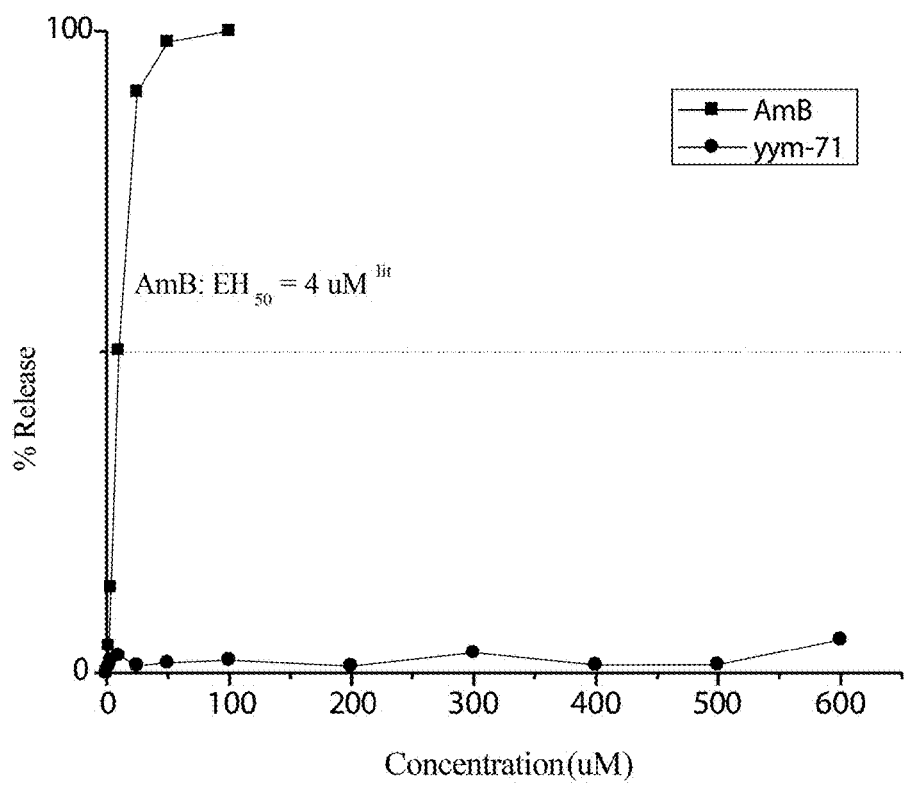
FIG. 9 compares the hemolytic activity of AmphB versus conjugate YYM-71 at various concentrations.
Figure 10:
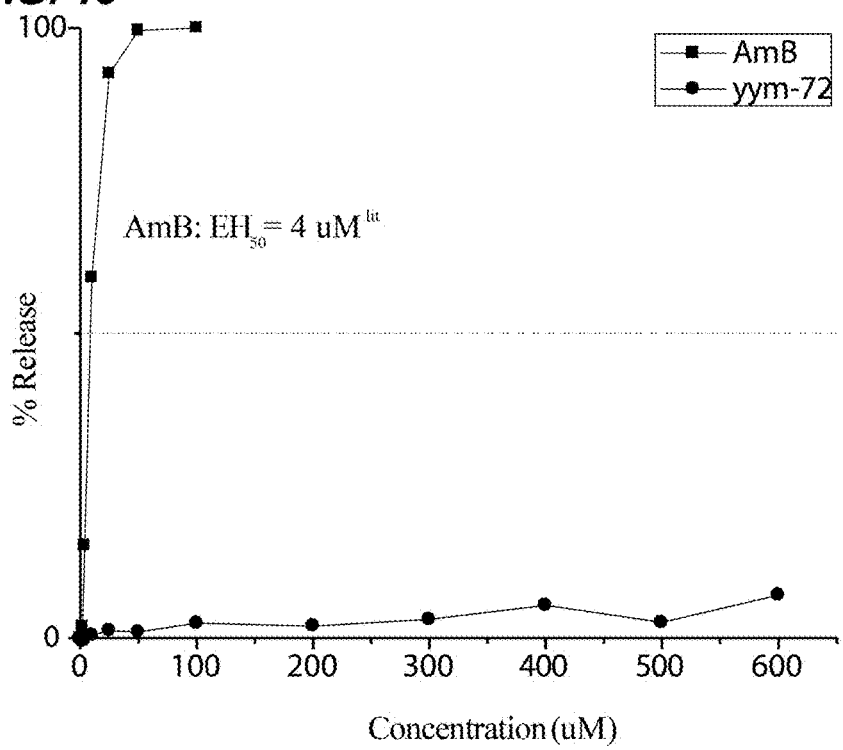
FIG. 10 compares the hemolytic activity of AmphB versus conjugate YYM-72 at various concentrations.

Hemolytic activities were tested per the procedures of Example 2 herein. FIG. 7 shows a plot of percent release of hemoglobin from sheep red blood cells as a function of concentration of AmphB (■) and YYM-69 (•) at 37° C. in PBS, pH 7.4. FIG. 8 shows a plot of percent release of hemoglobin from sheep red blood cells as a function of concentration of AmB (■) and YYM-70 (•) at 37° C. in PBS, pH 7.4. FIG. 9 shows a plot of percent release of hemoglobin from sheep red blood cells as a function of concentration of AmB (■) and YYM-71 (•) at 37° C. in PBS, pH 7.4. FIG. 10 shows a plot of percent release of hemoglobin from sheep red blood cells as a function of concentration of AmphB (■) and YYM-72 (•) at 37° C. in PBS, pH 7.4. YYM-72 has a similar structure to that of YYM-70 but differs in that it has two additional $CH_2$ groups in its linker. As is apparent from the hemolytic activities, 1b (YYM-69) and 1c (YYM-71) have negligible hemolytic activities at concentrations as high as 400 µM. However, 1a (YYM-70) shows significant hemolytic activity at 100 µM but close to negligible hemolytic activity at 50 µM. YYM-72 shows negligible hemolytic activity up to concentrations of 500 µM.

Figure 11:
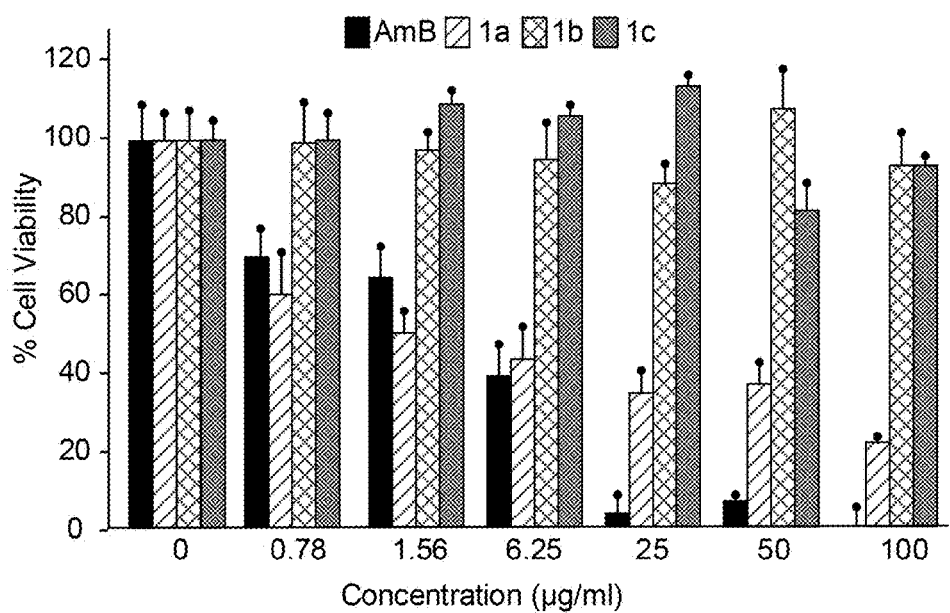
FIG. 11 shows data on the viability HEK293 cells in the presence of varying concentrations of AmphB and 1a (YYM-70), 1b (YYM-69) and 1c (YYM-71).

Toxicity towards HEK293 T Cells was tested per the procedures of Example 2 herein. FIG. 11 shows data on the viability HEK293 cells in the presence of varying concentrations of AmB and 1a (YYM-70), 1b (YYM-69) and 1c (YYM-71). As can be seen in comparing the antifungal activities of Table 4 with the toxicity against mammalian cells of FIG. 11 that the appropriate balance of anti-fungal activity and reduced toxicity must be obtained.

Comparison of the toxicity results with the hemolytic activities reveals a clear correlation; i.e., whereas 1b and 1c have negligible hemolytic activity and negligible cytotoxicity, the analogous conjugate, 1a shows significant hemolytic activity and significant toxicity towards HEK293 cells. Thus, when the hydrocarbon chain that separates the facial amphiphile from the Amphotericin B moiety becomes relatively short, the conjugate becomes more hemolytic and more cytotoxic.

Example 5: Animal Models

The study of a compound's antifungal activity in mice is important to understanding fungicidal and survival benefits in the mammalian system before advancing to human clinical trials. Mice have been the primary animal model for previous antifungal studies, and therefore provide important context and comparison.

For all animal models, experiments are conducted under approval of the Institutional Animal Care and Use Committee (IACUC) regulations. Mouse models utilize Balb/c or CD-1 males, 32-38 days old, 22-26 g weight, from Charles River Laboratories. Mice are acclimatized for 2-3 days prior to use, and then used as soon as possible thereafter. Animals are identified by temporary ink marking and are weighed daily. Animals are weighed at the outset of experiments, and any that are underweight by >2 standard deviations are not used.

Invasive Candidiasis: Experimentally infected mice develop disseminated candidiasis in a reliable and reproducible manner that substantially reproduces the invasive infection seen in humans. Fungal burden in the kidney, as well as survival, are well-accepted methods of determining extent of disease and for evaluating virulence, therapeutic, and diagnostic aspects of candidiasis. The bulk of the literature available on animal models of candidiasis was produced using tail vein injection in the murine model. In vivo toxicity testing employs a two dose toxicity study design, using 5 mice per group. Ten mice are used for each group receiving an experimental compound, allowing evaluation of statistical significance. Data from tissue burden studies will be analyzed using the unpaired T test or Kruskal-Wallis with Dunn correction for multiple comparisons. For studies using a tissue burden endpoint, inoculation consists of $1.8 \times 10^5$ cells of *Candida albicans*, verified by quantitative culture, injected via tail vein. Treatment is via the i.v., i.p. or oral (gavage) route for 7 days. Tissue burden in kidney is evaluated by quantitative culture per gram of tissue on day 8, by weighing organs and culturing serially diluted homogenates. These tissue burden studies permit detection of drug efficacy that may not be evident by using a survival endpoint.

Cryptococcosis mice are infected via tail vein injection of $5 \times 10^4$ *C. neoformans* cells. Inocula are verified by quantitative culture. Animals are identified by temporary ink marking, assigned to groups of 10 mice. Test compounds will be dosed starting on the day of infection. Initial studies will employ i.v., i.p. or oral (gavage) dosing (depending on the compound and the vehicle). Antifungal compounds are given for a period of 7 days. Dosages for experimental drugs will vary based on half-life and maximum tolerated dose data, but, for example, amphotericin B typically is given as i.v. for 7 days. On day 8, the lung and brain are evaluated by quantitative culture per gram of tissue, by weighing organs and culturing serially diluted homogenates. These tissue burden studies permit detection of drug efficacy that may not be evident by using a survival endpoint.

Example 6: Passage of Conjugates Through the BBB

Many drugs that have the potential for treating diseases of the brain are ineffective due to their limited ability to cross this barrier. Most drugs that can cross the BBB do so by passive transport—a process that usually favors small and lipophilic molecules. As discussed hereinabove, one example of a drug whose efficacy in the CNS is limited due to poor BBB—transport is Amphotericin B.

According to the classic "size rule", passive transport across the Blood Brain Barrier (BBB) requires a MW of <~400 Da (1 Da=1 g/mol). Successful treatment of infections in and of the brain through the use of systemically delivered drugs requires that the drug be able to sufficiently cross the BBB to achieve a therapeutic effect. AmphB has a MW of 924.08 Da (or g/mol), which affects its ability to cross the BBB. The present inventors undertook to determine whether molecular conjugates having a MW in excess of 400 Da would be able to cross the BBB.

In preliminary in vivo studies, antifungal activity was found in the brain and lung when VJ-1138 was administered, intraperitoneally, as a DMSO solution. In the model, CD1 male mice (20-25 g) were first infected with 50,000 *Cryptococcus neoformans* cells via tail vein injection, and were either left untreated (A, a control group), or immediately treated with intraperitoneal injections of (B) a DMSO solution of VJ-1138, (70 mg/kg/day), or (C) fungizone [i.e., an optimized pharmaceutical formulation consisting of AmB plus sodium deoxycholate—(3 mg/kg/day)]. The mice were then sacrificed 7 days later for quantitative culture of brain and lung, with cryptococcal cells per gram tissue being expressed as logarithmic values (log 10). Mean values for each group were compared using the t-test. The mean brain burden for A, B, and C were 8.22, 7.66, and 3.36, respectively. Mean lung burden for these mice were 6.34, 5.10, and 2.33, respectively. The lung and brain tissue burdens for the mice treated with B, when compared to the untreated mice, were found to be statistically significant using conventional criteria (p<0.0001 and p=0.0083, respectively).

Recently evidence has been adduced that fungal infections may contribute to Alzheimer's Disease (AD). Pisa, D., et al. Different Brain Regions are Infected with Fungi in Alzheimer's Disease. *Scientific Reports* 5:15015 (2015) 1-13. In the Pisa study, fungi were found in the brains of all eleven AD patients studied while none were found in the 10 controls. The existence of fungal infection in AD patients may be causative or contributory or may be due to a poor adaptive immune response in elderly patients. However, whether causative or consequential, fungal infection in the brain are associated with considerable morbidity. In one embodiment, anti-fungal conjugates are provided for treating Alzheimer's Disease by permitting the improved BBB-transport of anti-fungal drugs and reduced systemic toxicity, which allows for increased systemic doses and concomitant increased concentration in the brain.

Statements of the Disclosure include:

Statement 1: A compound comprising a polyene macrolide antibiotic; and a molecular umbrella bound to the polyene macrolide antibiotic, the molecular umbrella comprising: at least two facial amphiphiles bound to an amphiphile linking agent; and a non-cleavable linker bound to the amphiphile linking agent and the polyene macrolide antibiotic.

Statement 2: A compound according to Statement 1, wherein the non-cleavable linker consists of a hydrocarbon chain.

Statement 3: A compound according to Statement 2, wherein the hydrocarbon chain is a $C_3$-$C_{15}$ alkyl.

Statement 4: A compound according to Statement 1, wherein the non-cleavable linker consists of a polyether.

Statement 5: A compound according to any one of Statements 1-4, wherein the non-cleavable linker is bound to the amphiphile linking agent and the polyene macrolide antibiotic via amide bonds.

Statement 6: A compound according to any one of Statements 1-5, wherein the polyene macrolide antibiotic is any one of amphotericin B, nystatin, mycoheptin, candicidin, perimycin, and pimaricin, or any derivative thereof.

Statement 7: A compound according to any one of Statements 1-6, wherein each of the at least two facial amphiphiles is a sterol or facially amphiphilic derivative thereof; and the at least two facial amphiphiles are bound to the amphiphile linker via amide bonds.

Statement 8: A compound according to Statement 7, wherein the sterol is any one of cholic acid, deoxycholic acid, chenodeoxycholic acid, lithocholic acid, and amphiphilic derivatives thereof.

Statement 9: A compound according to any one of Statements 1-6, wherein at least one of the at least two facial amphiphiles has the following structure:

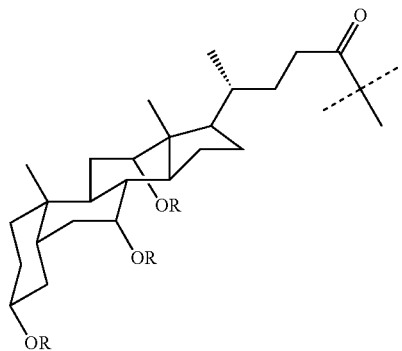

wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_xCO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 10: A compound according to any one of Statements 1-6, wherein at least one of the at least two facial amphiphiles has the following structure:

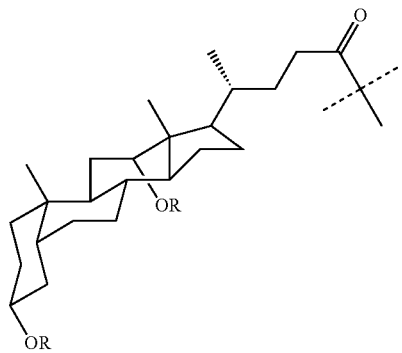

wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 11: A compound according to any one of Statements 1-6, wherein at least one of the at least two facial amphiphiles has the following structure:

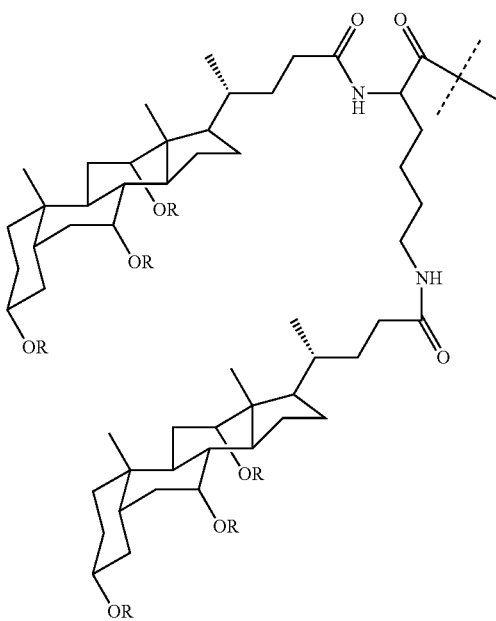

wherein each R is any one of H, CONH(CH$_2$)$_x$NH$_2$, CH$_2$COH(CH$_2$)$_x$OH, CH$_2$OH, (CH$_2$)$_x$OH, CH$_2$COOH, (CH$_2$)$_x$COOCH$_3$, (CH$_2$)$_x$COO(CH$_2$)$_y$CH$_3$, (CH$_2$)$_x$CHO, (CH$_2$)$_x$COCH$_3$, (CH$_2$)$_x$(CO(CH$_2$)$_y$CH$_3$ CONH(CH$_2$)$_x$NH$_3$Cl, CH$_2$NH$_2$, (CH$_2$)$_x$NH$_2$, (CH$_2$)$_x$NH(CH$_2$)$_y$NH$_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 11: A compound according to any one of Statements 1-6, wherein at least one of the at least two facial amphiphiles has the following structure:

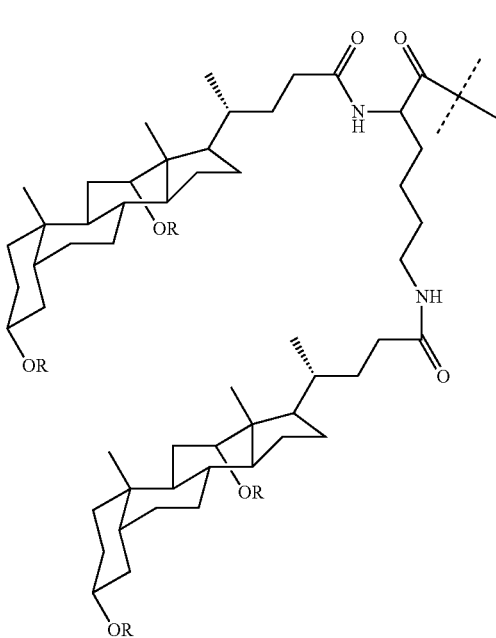

wherein each R is any one of H, CONH(CH$_2$)$_x$NH$_2$, CH$_2$COH(CH$_2$)$_x$OH, CH$_2$OH, (CH$_2$)$_x$OH, CH$_2$COOH, (CH$_2$)$_x$COOCH$_3$, (CH$_2$)$_x$COO(CH$_2$)$_y$CH$_3$, (CH$_2$)$_x$CHO, (CH$_2$)$_x$COCH$_3$, (CH$_2$)$_x$(CO(CH$_2$)$_y$CH$_3$ CONH(CH$_2$)$_x$NH$_3$Cl, CH$_2$NH$_2$, (CH$_2$)$_x$NH$_2$, (CH$_2$)$_x$NH(CH$_2$)$_y$NH$_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 13: A compound comprising a polyene macrolide antibiotic; and a facial amphiphile bound to the polyene macrolide antibiotic via a non-cleavable linker.

Statement 14: A compound according to Statement 13, wherein the non-cleavable linker consists of a hydrocarbon chain.

Statement 15: A compound according to Statement 14, wherein the hydrocarbon chain is a linear alkane ranging from 3 to 15 carbon groups.

Statement 16: A compound according to Statement 13, wherein the non-cleavable linker consists of a polyether.

Statement 17: A compound according to any one of Statements 13-16, wherein the non-cleavable linker is bound to the polyene macrolide antibiotic via an amide bond.

Statement 18: A compound according to any one of Statements 13-17, wherein the polyene macrolide antibiotic is any one of amphotericin B, nystatin, mycoheptin, candicidin, perimycin, and pimaricin, or any derivative thereof.

Statement 19: A compound according to any one of Statements 13-18, wherein the facial amphiphile is sterol or amphiphilic derivative thereof; and the facial amphiphile is bound to the non-cleavable linker via an amide bond.

Statement 20: A compound according to Statement 19, wherein the sterol is any one of cholic acid, deoxycholic acid, chenodeoxycholic acid, lithocholic acid, and amphiphilic derivatives thereof.

Statement 21: A compound according to any one of Statements 13-18, wherein the facial amphiphile has the following structure:

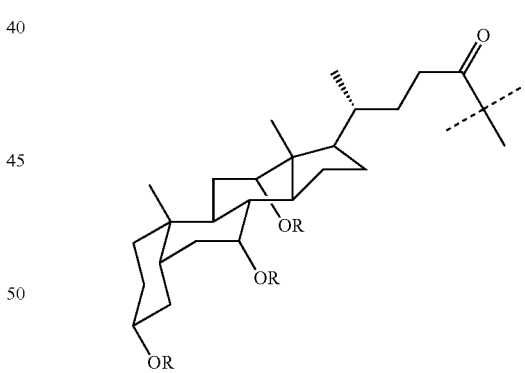

wherein each R is any one of H, CONH(CH$_2$)$_x$NH$_2$, CH$_2$COH(CH$_2$)$_x$OH, CH$_2$OH, (CH$_2$)$_x$OH, CH$_2$COOH, (CH$_2$)$_x$COOCH$_3$, (CH$_2$)$_x$COO(CH$_2$)$_y$CH$_3$, (CH$_2$)$_x$CHO, (CH$_2$)$_x$COCH$_3$, (CH$_2$)$_x$(CO(CH$_2$)$_y$CH$_3$ CONH(CH$_2$)$_x$NH$_3$Cl, CH$_2$NH$_2$, (CH$_2$)$_x$NH$_2$, (CH$_2$)$_x$NH(CH$_2$)$_y$NH$_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 22: A compound according to any one of Statements 13-18, wherein the facial amphiphile has the following structure:

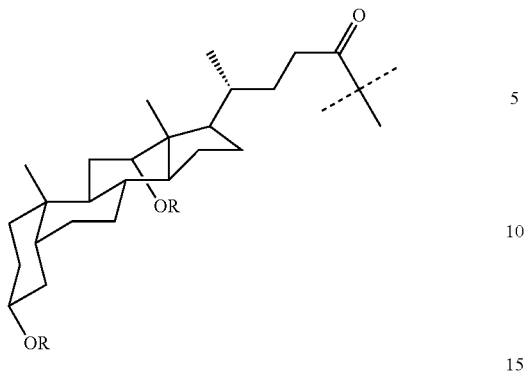

wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 23: A compound comprising a polyene macrolide antibiotic; and a molecular umbrella having any one of the following chemical structures:

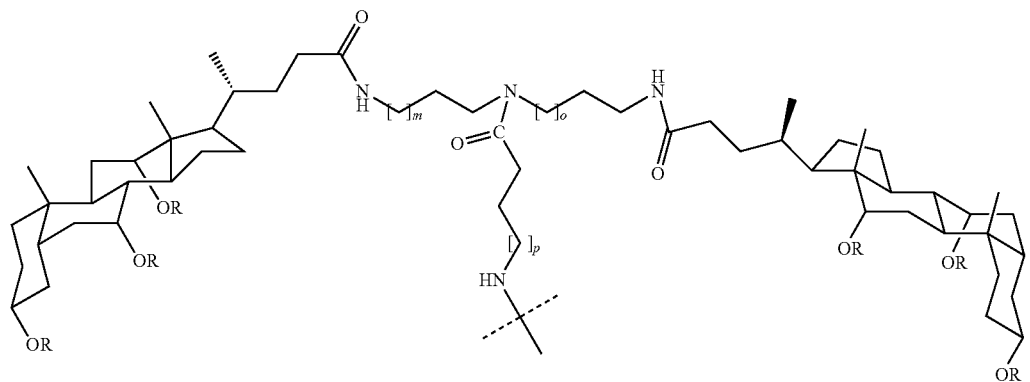

wherein m and o are integers ranging from 1 to 7, p is an integer ranging from 1 to 13, and wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, and, where x and y are integers; or wherein OR is any one of a phosphate, a phosphate ester, a phosphonate, a sulfate, a sulfonate;

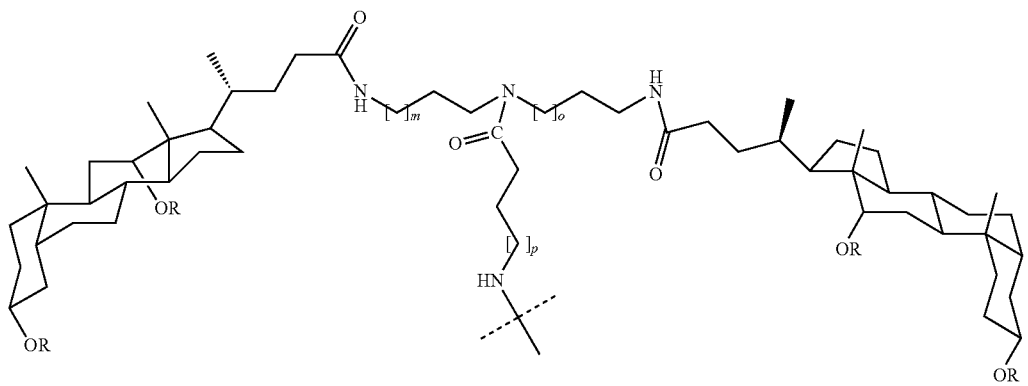

wherein m and o are integers ranging from 1 to 7, p is an integer ranging from 1 to 13, and wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, and, where x and y are integers; or wherein OR is any one of a phosphate, a phosphate ester, a phosphonate, a sulfate, a sulfonate;

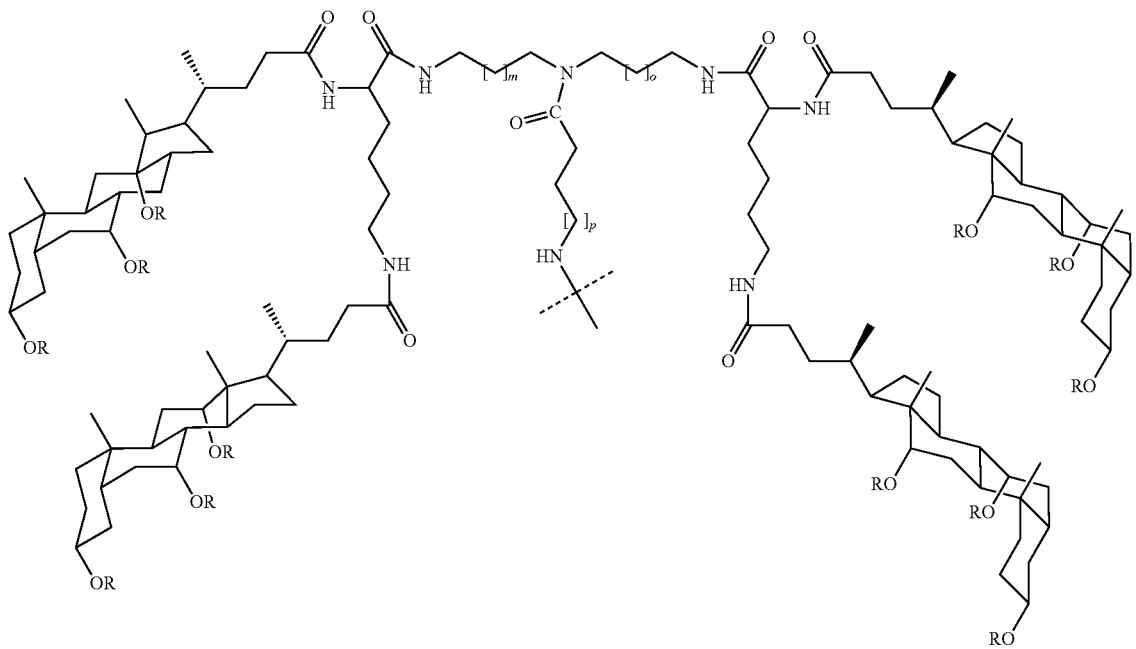

wherein m and o are integers ranging from 1 to 7, p is an integer ranging from 1 to 13, and wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate; and

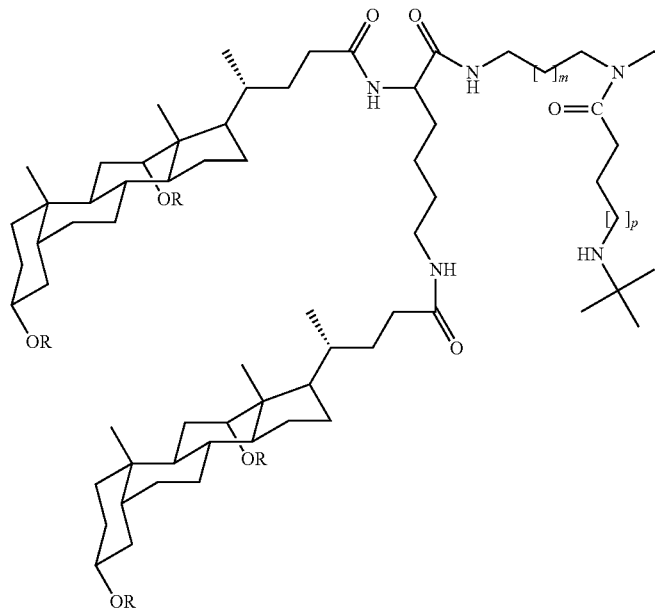

wherein m and o are integers ranging from 1 to 7, p is an integer ranging from 1 to 13, and wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 24: A compound according to Statement 23, wherein the molecular umbrella is bound to the polyene macrolide antibiotic via an amide bond.

Statement 25: A compound according to any one of Statements 23-24, wherein the polyene macrolide antibiotic is any one of amphotericin B, nystatin, mycoheptin, candicidin, perimycin, and pimaricin, or any derivative thereof.

Statement 26: A compound comprising a polyene macrolide antibiotic; and a molecular float having any one of the following chemical structures:

wherein m is an integer ranging from 1 to 8;
wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate; and wherein m is an integer ranging from 1 to 8;
wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_x(CO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

Statement 27: A compound according to Statement 26, wherein the molecular float is bound to the polyene macrolide antibiotic via an amide bond.

Statement 28: A compound according to any one of Statements 26-27, wherein the polyene macrolide antibiotic is any one of amphotericin B, nystatin, mycoheptin, candicidin, perimycin, and pimaricin, or any derivative thereof.

Statement 29: A formulation comprising a compound according to any one Statements 1-27.

Statement 30: A formulation for oral administration comprising a compound according to any one Statements 1-27.

Statement 31: A formulation comprising a compound according to any one Statements 1-27, the formulation in the form of a tablet.

Statement 32: A formulation comprising a solution or suspension of a compound according to any one Statements 1-27.

Statement 33: A transdermal patch comprising a formulation, the formulation including a compound according to any one Statements 1-27.

Statement 34: A formulation comprising a compound according to any one Statements 1-27, the formulation in the form of a suppository.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A compound comprising:
   a polyene macrolide antibiotic; and
   a single facial amphiphile bound to the polyene macrolide antibiotic via a non-cleavable linker;
   wherein the facial amphiphile is sterol or amphiphilic derivative thereof; and the facial amphiphile is bound to the non-cleavable linker via an amide bond.

2. The compound of claim 1, wherein the non-cleavable linker consists of a hydrocarbon chain.

3. The compound of claim 2, wherein the hydrocarbon chain is a linear alkane ranging from 3 to 15 carbon groups.

4. The compound of claim 1, wherein the non-cleavable linker consists of a polyether.

5. The compound of claim 1, wherein the polyene macrolide antibiotic is any one of amphotericin B, nystatin, mycoheptin, candicidin, perimycin, and pimaricin, or any derivative thereof.

6. The compound of claim 1, wherein the sterol is any one of cholic acid, deoxycholic acid, chenodeoxycholic acid, lithocholic acid, and amphiphilic derivatives thereof.

7. The compound of claim 1, wherein the facial amphiphile has the following structure:

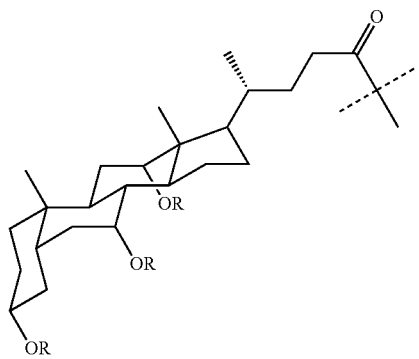

wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_xCO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

8. The compound of claim 1, wherein the facial amphiphile has the following structure:

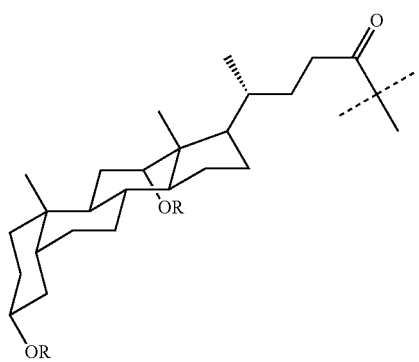

wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_xCO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or wherein OR is any one of a phosphate, a phosphate ester, a phosphonate, a sulfate, a sulfonate.

9. A compound comprising:
   a polyene macrolide antibiotic; and
   a molecular float having any one of the following chemical structures:

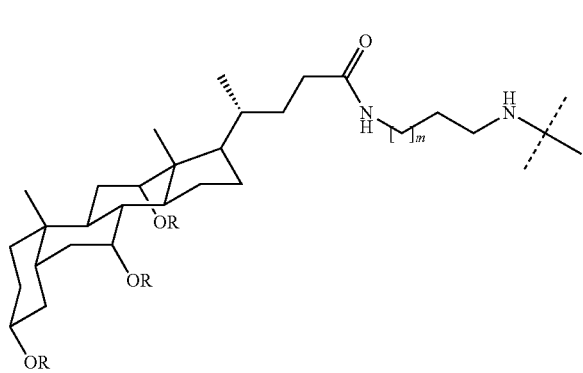

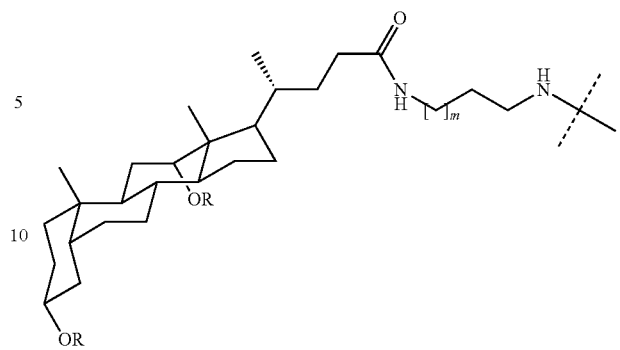

wherein m is an integer ranging from 1 to 8;
wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_xCO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or
wherein OR is any one of a phosphate, a phosphate ester, a phosphonate, a sulfate, a sulfonate; and wherein m is an integer ranging from 1 to 8;
wherein each R is any one of H, $CONH(CH_2)_xNH_2$, $CH_2COH(CH_2)_xOH$, $CH_2OH$, $(CH_2)_xOH$, $CH_2COOH$, $(CH_2)_xCOOCH_3$, $(CH_2)_xCOO(CH_2)_yCH_3$, $(CH_2)_xCHO$, $(CH_2)_xCOCH_3$, $(CH_2)_xCO(CH_2)_yCH_3$ $CONH(CH_2)_xNH_3Cl$, $CH_2NH_2$, $(CH_2)_xNH_2$, $(CH_2)_xNH(CH_2)_yNH_2$, an alkyl phosphate, an alkyl phosphate ester, an alkyl phosphonate, an alkyl sulfate, an alkyl sulfonate, a sulfone, a sulfonamide, where x and y are integers; or
wherein OR is any one of a phosphate, a phosphate ester, a phosphonate, a sulfate, a sulfonate.

10. The compound of claim 9, wherein the molecular float is bound to the polyene macrolide antibiotic via an amide bond.

11. The compound of claim 9, wherein the polyene macrolide antibiotic is any one of amphotericin B, nystatin, mycoheptin, candicidin, perimycin, and pimaricin, or any derivative thereof.

* * * * *

UNITED STATES PATENT AND TRADEMARK OFFICE
CERTIFICATE OF CORRECTION

PATENT NO. : 10,322,187 B2
APPLICATION NO. : 15/233679
DATED : June 18, 2019
INVENTOR(S) : Steven L Regen, Vaclav Janout and Yuming Yu It is certified that error appears in the above-identified patent and that said Letters Patent is hereby corrected as shown below:

In the Specification

In the Description:

Column 1, Lines 15-18: change "This work was supported in part by the following United States Government grants: R01 GM100962 from the National Institutes of Health. The Government has or may have certain rights in this invention." to "This invention was made with government support under R01 GM100962 awarded by the National Institutes of Health. The government has certain rights in the invention."

Signed and Sealed this
Twelfth Day of July, 2022

Katherine Kelly Vidal
*Director of the United States Patent and Trademark Office*